US010888060B1

(12) United States Patent
Reel

(10) Patent No.: US 10,888,060 B1
(45) Date of Patent: Jan. 12, 2021

(54) HEMP PLANT NAMED 'KIRSCHE'

(71) Applicant: Charlotte's Web, Inc., Boulder, CO (US)

(72) Inventor: Keri Reel, Lafayette, CO (US)

(73) Assignee: Charlotte's Web, Inc., Boulder, CO (US)

( * ) Notice: Subject to any disclaimer, the term of this patent is extended or adjusted under 35 U.S.C. 154(b) by 0 days.

(21) Appl. No.: 16/895,569

(22) Filed: Jun. 8, 2020

Related U.S. Application Data

(60) Provisional application No. 62/978,399, filed on Feb. 19, 2020.

(51) Int. Cl.
*A01H 5/12* (2018.01)
*A01H 6/28* (2018.01)

(52) U.S. Cl.
CPC .............. *A01H 6/28* (2018.05); *A01H 5/12* (2013.01)

(58) Field of Classification Search
CPC ..................................................... A01H 6/28
See application file for complete search history.

(56) References Cited

U.S. PATENT DOCUMENTS

| | | |
|---|---|---|
| 9,095,554 B2 | 8/2015 | Lewis et al. |
| PP27,475 P2 | 12/2016 | Kubby |
| PP30,639 P2 | 7/2019 | Stanley |
| 10,653,085 B1 | 5/2020 | Stanley et al. |
| 10,736,295 B1 | 8/2020 | Stanley et al. |
| 2013/0291219 A1 | 10/2013 | Larkins et al. |
| 2014/0072693 A1 | 3/2014 | Waycott |
| 2014/0223669 A1 | 8/2014 | Corona, III et al. |
| 2014/0224707 A1 | 8/2014 | Haroun et al. |
| 2014/0228479 A1 | 8/2014 | Darnaud et al. |
| 2017/0202170 A1 | 7/2017 | Lewis et al. |
| 2018/0295804 A1 | 10/2018 | Muck |
| 2019/0037792 A1 | 2/2019 | Leo et al. |
| 2019/0067414 A1 | 2/2019 | Cheng et al. |

FOREIGN PATENT DOCUMENTS

| | | |
|---|---|---|
| WO | WO 2020/010102 | 1/2020 |
| WO | WO 2020/132206 | 6/2020 |

OTHER PUBLICATIONS

Bertoli, A., et al. Industrial Crops and Products (2010), vol. 32, pp. 329-337. (Year: 2010).*
(Charlotte's Web Holdings, Inc.) Charlotte's Web 2019 Harvest Delivers 10% Increase in Yield and 22% Increase in CBD Potency due to Proprietary Genetics, Mar. 4, 2020, 4 pages.
Clarke et al., "Cannabis domestication, breeding history, present-day genetic diversity, and future prospects." Critical Reviews in Plant Sciences, 2016, 35(5-6): 293-327.
CW Hemp Supply Company. LINDOREA Fact Sheet. Publication date unknown. pp. 1-2. Obtained Jul. 2, 2020 from http://www.cwhempsupplyco.com/l/6998 93/2020-04-08/gjjbv.
Giese et al., "Development and Validation of a Reliable and Robust Method for the Analysis of Cannabinoids and Terpenes in Cannabis," Journal of AOAC International vol. 98, No. 6, 2015.
Ingold, "Desperate Journey: CBD in Colorado, Story 4, Pushing Ahead," The Denver Post Dec. 9, 2014, pp. 1-8. (Year: 2014).
International Search Report and Written Opinion dated Apr. 28, 2020, for International Application No. PCT/US2019/067414, 9 pages.
International Search Report and Written Opinion dated Sep. 9, 2020, for International Application No. PCT/US2020/036652, 9 pages.
Kentucky Department of Agriculture. Hemp Program summary of varieties: Including varieties of concern and prohibited varieties. Published Jan. 17, 2020. pp. 1-11.
Leinow & Birnbaum, foreword by Michael H. Moskowitz, MD., "CBD: A Patient's Guide to Medicinal Cannabis," sponsored by published by the Society for the Study of Native Arts and Sciences (dba North Atlantic Books) Chapter 8, (2017), 23 pages.
Quarles, Kentucky Department of Agriculture, "Industrial Hemp Research Pilot Program Summary of Varieties: Including Varieties of Concern and Prohibited Varieties," retrieved on Jul. 11, 2018, retrieved from the Internet at http://www.kyagr.com/marketing/documents/ HEMP_LH_Summary-of-Varieties.pdf, pp. 1-4, 2018. (Year: 2018).
State of Hawaii. Approved Varietals. Published Dec.12, 2019. pp. 1-2. Obtained Jul. 2, 2020 from https://hdoa.hawaii.gov/ hemp/approved-varietals/.
UPOV, International Union for the Protection of New Varieties of Plants, Explanatory Notes on Essentially Derived Varieties Under the 1991 Act of the UPOV Convention, Apr. 6, 2017, 13 pages.

* cited by examiner

*Primary Examiner* — Russell Kallis
(74) *Attorney, Agent, or Firm* — Cooley LLP

(57) ABSTRACT

The present disclosure provides a new and distinct hemp cultivar designated 'KIRSCHE'. The present disclosure relates to seeds of the hemp plant 'KIRSCHE,' to plants and parts of the hemp plant 'KIRSCHE,' and to methods for producing a hemp plant by crossing the hemp plant 'KIRSCHE' with itself or other *Cannabis* plants. The disclosure further relates to the morphological and physiological characteristics of the new and distinct hemp cultivar and its uses.

29 Claims, 5 Drawing Sheets

HEMP PLANT NAMED 'KIRSCHE'

CROSS-REFERENCE TO RELATED APPLICATIONS

This application claims priority to and the benefit of U.S. Provisional Application No. 62/978,399 filed on Feb. 19, 2020, the entire contents of which are incorporated herein by reference in their entirety for all purposes.

FIELD

The disclosure relates to a hemp varieties, hemp extracts, CBD-containing compositions, and methods of producing and using the same.

BACKGROUND

*Cannabis* is a genus of flowering plants that includes at least three species, *Cannabis sativa, Cannabis indica*, and *Cannabis ruderalis* as determined by plant phenotypes and secondary metabolite profiles. Hemp, also known as industrial hemp, is a type of *Cannabis* plant grown specifically for the industrial uses of its derived products. In the United States, *Cannabis* is classified as hemp if it accumulates no more than three-tenths of one percent (i.e., 0.3%) concentration of tetrahydrocannabinol (THC) at harvest maturity. Hemp plants can also accumulate high levels of cannabidiol (CBD), which is used in a variety of consumer goods, including food, drinks, dietary supplements and cosmetics.

Hemp production however, remains challenging for farmers. The presence of a single male flower in a hemp field can ruin an entire crop by fertilizing the valuable female flowers. Large scale hemp growth also requires hemp varieties with uniform growth to avoid early or late maturation of a significant portion of the crop. Feminized seeds for high CBD producing lines with resistance to common pests are highly desirable, but not yet widely available.

Thus, there remains a need for new hemp varieties to meet the growing demand for fiber and CBD-based products.

BRIEF SUMMARY

This disclosure relates to a new and distinctive hemp cultivar designated as 'KIRSCHE.' In some embodiments, the 'KIRSCHE' is a *Cannabis sativa* L. plant.

The inventors reproduced the 'KIRSCHE' cultivar through strategic crosses and selections from proprietary lines. The 'KIRSCHE' plant is maintained as a hybrid seed produced by crossing two parental lines maintained at the inventors' greenhouses, nurseries, fields and/or facilities in Colorado.

The present disclosure provides a new and distinctive hemp variety designated as 'KIRSCHE'. The present disclosure relates to the seeds of hemp variety 'KIRSCHE,' to the plants or parts of hemp variety 'KIRSCHE,' to the plant cells of hemp variety 'KIRSCHE', to the plants or plant parts or plant cells having all of the essential physiological and morphological characteristics of hemp variety 'KIRSCHE' and to plants or plant parts or plant cells having all of the essential physiological and morphological characteristics of plant cells listed in Tables 1-5, including, but not limited to, as determined at the 5% significance level when grown in the same environmental conditions, including when grown side-by-side with a comparison or check *Cannabis* and/or hemp plant.

The present disclosure relates to methods for producing a hemp plant and/or seed, by crossing the hemp variety 'KIRSCHE' with itself or another *Cannabis* and/or hemp plant. A further aspect relates to hybrid hemp plants, and hemp seeds produced by crossing the hemp variety 'KIRSCHE' with a *Cannabis* and/or hemp plant.

Another aspect of the present disclosure is also directed to a method of producing a cannabinoid extract comprising contacting plants of the hemp variety 'KIRSCHE' with a solvent or heat, and producing the cannabinoid extract.

In some embodiments, the present disclosure teaches a seed, plant, plant part, or plant cell of hemp plant variety designated 'KIRSCHE', wherein representative seed of the variety has been deposited under NCMA No. 202005042. In some embodiments, the present disclosure teaches that the plant part is an inflorescence and/or a flower.

In some embodiments, the present disclosure teaches a hemp plant or a plant part or a plant cell thereof, having all of the essential physiological and morphological characteristics of the hemp plant variety designated 'KIRSCHE' listed in Tables 1-5 including, but not limited to, as determined at the 5% significance level when grown in the same environmental conditions, including when grown side-by-side with a comparison or check *Cannabis* and/or hemp plant. In some embodiments, the present disclosure teaches a hemp plant, or a plant part or a plant cell thereof, having all of the essential physiological and morphological characteristics of the hemp plant of the present disclosure.

In some embodiments, the present disclosure teaches a hemp plant, or a plant part or a plant cell thereof, having all of the essential physiological and morphological characteristics of the hemp plant variety designated 'KIRSCHE', wherein a representative sample of seed of said variety was deposited under NCMA No. 202005042.

In some embodiments, the present disclosure teaches a tissue culture of regenerable cells produced from the plant, plant part or plant cell of the present disclosure, wherein a new plant regenerated from the tissue culture has all of the essential morphological and physiological characteristics of the hemp plant variety designated 'KIRSCHE' listed in Tables 1-5 when grown under the same environmental conditions. In some embodiments, the present disclosure teaches a hemp plant regenerated from the tissue culture of the present disclosure, said plant having all the essential morphological and physiological characteristics of the hemp of the present disclosure. In some embodiments, the present disclosure teaches a hemp plant regenerated from the tissue culture, wherein the regenerated plant has all of the characteristics of the hemp plant variety designated 'KIRSCHE', wherein a representative sample of seed of said variety was deposited under NCMA No. 202005042.

In some embodiments, the present disclosure teaches a method for producing a hemp seed, comprising a) selfing the hemp plant of the present disclosure, and b) harvesting the resultant hemp seed. In some embodiments, the present disclosure teaches a hemp seed produced by the method of the present disclosure.

In some embodiments, the present disclosure teaches a method for producing a hemp seed comprising crossing the hemp plant of the present disclosure with a second, distinct plant. In some embodiments, the present disclosure teaches an $F_1$ hemp seed produced by the method of the present disclosure. In some embodiments, the present disclosure teaches an $F_1$ hemp plant, or a part or a plant cell thereof, produced by growing the seed of the present disclosure.

In some embodiments, the present disclosure teaches a method of producing a hemp plant derived from the variety 'KIRSCHE,' comprising: a) crossing the plant of the present disclosure, with itself or a second plant to produce progeny seed; b) growing the progeny seed to produce a progeny plant and crossing the progeny plant with itself or a second plant to produce further progeny seed; and, optionally c) repeating step (b) one or more times to produce the hemp plant derived from the variety 'KIRSCHE'.

In some embodiments, the present disclosure teaches a method of producing a hemp plant derived from the variety 'KIRSCHE', further comprising crossing the hemp plant derived from the variety 'KIRSCHE,' with a plant of a different genotype to produce seed of a hybrid plant derived from the hemp variety 'KIRSCHE.'

In some embodiments, the present disclosure teaches a method for producing nucleic acids, comprising isolating nucleic acids from the seed, plant, plant part, or plant cell of the present disclosure.

In some embodiments, the present disclosure teaches a hemp plant comprising a single locus conversion and otherwise essentially all the essential morphological and physiological characteristics of the hemp plant 'KIRSCHE' when grown in the same environmental conditions. In some embodiments, the present disclosure teaches that the single locus conversion confers said plant with herbicide resistance. In some embodiments, the present disclosure teaches that the single locus conversion is an artificially mutated gene or nucleotide sequence. In some embodiments, the present disclosure teaches that the single locus conversion is a gene that has been modified through the use of breeding techniques taught in the present disclosure.

In some embodiments, the present disclosure teaches a cultivar of hemp designated 'KIRSCHE' as described and detailed in the present disclosure.

In some embodiments, the present disclosure teaches a method of producing a cannabinoid extract, said method comprising the steps (a) contacting the plant of the present disclosure with a solvent or heat, thereby producing a cannabinoid extract.

In some embodiments, the present disclosure teaches a dry, non-viable plant part, wherein representative seed of hemp plants producing said dry plant parts has been deposited under NCMA No. 202005042.

In some embodiments, the present disclosure teaches an assemblage of dry, non-viable female inflorescences from a hemp plant variety designated 'KIRSCHE' wherein representative seed the variety has been deposited under NCMA No. 202005042. In some embodiments, the present disclosure teaches that a dry, non-viable plant part is an inflorescence and/or a flower.

In some embodiments, the present disclosure teaches a hemp plant of the present disclosure is asexually reproduced. In some embodiments, the present disclosure teaches a hemp plant of the present disclosure is capable of producing an asexual clone of said hemp plant. In some embodiments, the present disclosure teaches that the asexual clone is capable of producing said hemp plant taught in the present disclosure.

A further embodiment relates to a method for developing a hemp plant in a hemp plant breeding program, comprising applying plant breeding techniques comprising crossing, recurrent selection, mutation breeding, wherein said mutation breeding selects for a mutation that is spontaneous or artificially induced, backcrossing, pedigree breeding, marker enhanced selection, haploid/double haploid production, or transformation to the hemp plant of 'KIRSCHE', or its parts, wherein application of said techniques results in development of a hemp plant.

A further embodiment relates to a method of introducing a mutation into the genome of hemp plant 'KIRSCHE', said method comprising mutagenesis of the plant, or plant part thereof, of 'KIRSCHE', wherein said mutagenesis is selected from the group consisting of temperature, long-term seed storage, tissue culture conditions, ionizing radiation, chemical mutagens, and targeting induced local lesions in genomes, and wherein the resulting plant comprises at least one genome mutation and producing plants therefrom.

A further embodiment relates to a method of editing the genome of hemp plant 'Kirsche', wherein said method is selected from the group comprising zinc finger nucleases, transcription activator-like effector nucleases (TALENs), engineered homing endonucleases/meganucleases, and the clustered regularly interspaced short palindromic repeat (CRISPR)-associated protein9 (Cas9) system, and plants produced therefrom.

DESCRIPTION OF THE DRAWINGS

The accompanying photographs depict characteristics of the new 'KIRSCHE' plants as nearly true as possible reproductions. The overall appearance of the 'KIRSCHE' plants in the photographs may differ slightly from the color values described in the detailed botanical description of Tables 1-5.

DETAILED DESCRIPTION OF THE INVENTION

Figure 1:
FIG. 1 shows an overall view of the 'KIRSCHE' plant with main axis dominance close to floral maturity.
Figure 2:
FIG. 2 shows another overall view of the 'KIRSCHE' plant with main axis dominance close to floral maturity.
Figure 3:
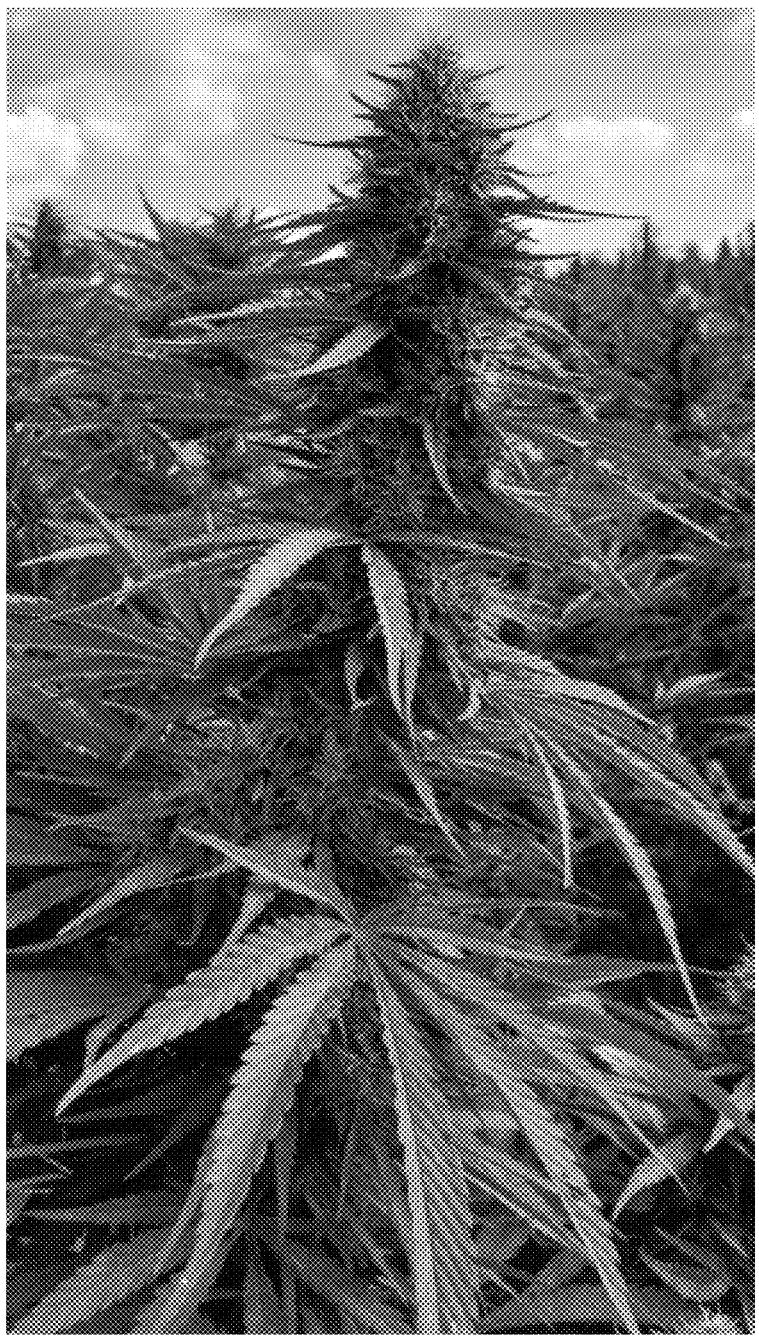
FIG. 3 shows a close view of upper part (including flowers) of the 'KIRSCHE' plant with main axis dominance close to floral maturity.
Figure 4:
FIG. 4 shows a close view of upper part (including flowers) of the 'KIRSCHE' plant with main axis dominance close to floral maturity.
Figure 5:
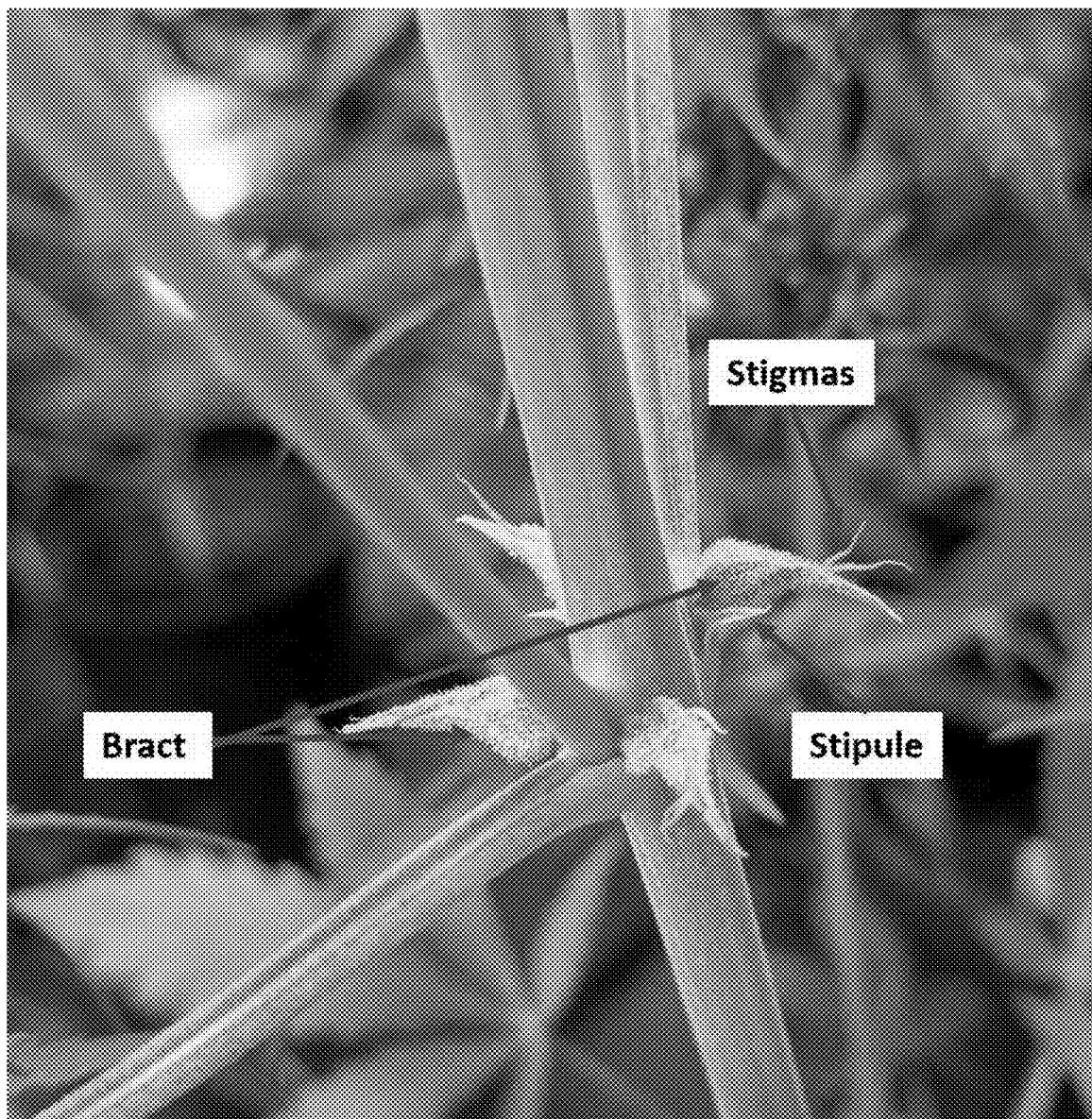
FIG. 5 shows a close view of an industrial hemp internode with emerging female inflorescences. Bract, stipule, and stigmas are labelled. The bract is the trichomated leaf structure enveloping the ovule. The stigma is the sticky antennae-like structure of the female inflorescence for catching pollen, which emerges from the bract opening. The stipule is a small, spike-like leaflet emerging under the bract from the peduncle.

All publications, patents and patent applications, including any drawings and appendices, are herein incorporated by reference to the same extent as if each individual publication or patent application was specifically and individually indicated to be incorporated by reference.

The following description includes information that may be useful in understanding the present disclosure. It is not an admission that any of the information provided herein is prior art or relevant to the presently claimed disclosures, or that any publication specifically or implicitly referenced is prior art.

Definitions

As used herein, the verb "comprise" is used in this description and in the claims and its conjugations are used in its non-limiting sense to mean that items following the word are included, but items not specifically mentioned are not excluded.

As used herein, the term "about" refers to plus or minus 10% of the referenced number, unless otherwise stated or otherwise evident by the context (such as when a range would exceed 100% of a possible value or fall below 0% of a possible value). For example, reference to an absolute content of a particular cannabinoid of "about 1%" means that that cannabinoid can be present at any amount ranging from 0.9% to 1.1% content by weight.

The disclosure provides *Cannabis* hemp plants. As used herein, the term "plant" refers to plants in the genus of *Cannabis* and plants derived thereof. Such as *Cannabis* plants produced via asexual reproduction, tissue culture, and via seed production.

The disclosure provides plant parts. As used herein, the term "plant part" refers to any part of a plant including but not limited to the embryo, shoot, root, stem, seed, stipule, leaf, petal, flower, inflorescence, bud, ovule, bract, trichome, branch, petiole, internode, bark, pubescence, tiller, rhizome, frond, blade, ovule, pollen, stamen, and the like. The two main parts of plants grown in some sort of media, such as soil or vermiculite, are often referred to as the "aboveground" part, also often referred to as the "shoots", and the "below-ground" part, also often referred to as the "roots". Plant parts may also include certain extracts such as kief or hash, which include *Cannabis* plant trichomes or glands. In some embodiments, plant part should also be interpreted as referring to individual cells from the plant.

As used herein, the term "plant cell" refers to any plant cell from a *Cannabis* plant. Plant cells of the present disclosure include cells from a *Cannabis* plant shoot, root, stem, seed, stipule, leaf, petal, inflorescence, bud, ovule, bract, trichome, petiole, internode. In some embodiments, the disclosed plant cell is from a *Cannabis* trichome.

The term "a" or "an" refers to one or more of that entity; for example, "a gene" refers to one or more genes or at least one gene. As such, the terms "a" (or "an"), "one or more" and "at least one" are used interchangeably herein. In addition, reference to "an element" by the indefinite article "a" or "an" does not exclude the possibility that more than one of the elements is present, unless the context clearly requires that there is one and only one of the elements.

The International Code of Zoological Nomenclature defines rank, in the nomenclatural sense, as the level, for nomenclatural purposes, of a taxon in a taxonomic hierarchy (e.g., all families are for nomenclatural purposes at the same rank, which lies between superfamily and subfamily). While somewhat arbitrary, there are seven main ranks defined by the international nomenclature codes: kingdom, phylum/division, class, order, family, genus, and species. Further taxonomic hierarchies used in this disclosure are described below.

The disclosure provides plant cultivars. As used herein, the term "cultivar" means a group of similar plants that by structural features and performance (i.e., essential morphological and physiological characteristics) can be identified from other cultivars within the same species. Furthermore, the term "cultivar" variously refers to a variety, strain or race of plant that has been produced by horticultural or agronomic techniques and is not normally found in wild populations. The terms cultivar, variety, strain and race are often used interchangeably by plant breeders, agronomists and farmers.

The term "variety" as used herein has identical meaning to the corresponding definition in the International Convention for the Protection of New Varieties of Plants (UPOV treaty), of Dec. 2, 1961, as Revised at Geneva on Nov. 10, 1972, on Oct. 23, 1978, and on Mar. 19, 1991. Thus, "variety" means a plant grouping within a single botanical taxon of the lowest known rank, which grouping, irrespective of whether the conditions for the grant of a breeder's right are fully met, can be i) defined by the expression of the characteristics resulting from a given genotype or combination of genotypes, ii) distinguished from any other plant grouping by the expression of at least one of the said characteristics and iii) considered as a unit with regard to its suitability for being propagated unchanged.

The disclosure provides methods for obtaining plant lines. As used herein, the term "line" is used broadly to include, but is not limited to, a group of plants vegetatively propagated from a single parent plant, via tissue culture techniques, or a group of inbred or hybrid plants which are genetically very similar due to descent from a common parent(s) (e.g., by selfing of a genetically stable cultivar. A plant is said to "belong" to a particular line if it (a) is a primary transformant (T0) plant regenerated from material of that line; (b) has a pedigree comprised of a T0 plant of that line; or (c) is genetically very similar due to common ancestry (e.g., via inbreeding or selfing). In this context, the term "pedigree" denotes the lineage of a plant, e.g. in terms of the sexual crosses affected such that a gene or a combination of genes, in heterozygous (hemizygous) or homozygous condition, imparts a desired trait to the plant.

As used herein, the term "inbreeding" refers to the production of offspring via the mating between relatives. The plants resulting from the inbreeding process are referred to herein as "inbred plants" or "inbreds."

The term single allele converted plant as used herein refers to those plants that are developed by a plant breeding technique called backcrossing wherein essentially all of the desired morphological and physiological characteristics of an inbred are recovered in addition to the single allele transferred into the inbred via the backcrossing technique.

The disclosure provides samples. As used herein, the term "sample" includes a sample from a plant, a plant part, a plant cell, or from a transmission vector, or a soil, water or air sample.

The disclosure provides offspring. As used herein, the term "offspring" refers to any plant resulting as progeny from a vegetative or sexual reproduction from one or more parent plants or descendants thereof. For instance, an offspring plant may be obtained by cloning or selfing of a parent plant or by crossing two parent plants and include selfings as well as the $F_1$ or $F_2$ or still further generations. An $F_1$ is a first-generation offspring produced from parents at least one of which is used for the first time as donor of a trait, while offspring of second generation ($F_2$) or subsequent generations ($F_3$, $F_4$, etc.) are specimens produced from selfings of $F_1$'s, $F_2$'s etc. An $F_1$ may thus be (and usually is) a hybrid resulting from a cross between two true breeding parents (true-breeding is homozygous for a trait), while an $F_2$ may be (and usually is) an offspring resulting from self-pollination of said $F_1$ hybrids.

The disclosure provides methods for crossing a first plant with a second plant. As used herein, the term "cross," "crossing," "cross pollination" or "cross-breeding" refer to the process by which the pollen of one flower on one plant is applied (artificially or naturally) to the ovule (stigma) of a flower on another plant. Backcrossing is a process in which a breeder repeatedly crosses hybrid progeny, for example a first generation hybrid ($F_1$), back to one of the parents of the hybrid progeny. Backcrossing can be used to introduce one or more single locus conversions from one genetic background into another.

In some embodiments, the present disclosure provides methods for obtaining plant genotypes. As used herein, the term "genotype" refers to the genetic makeup of an individual cell, cell culture, tissue, organism (e.g., a plant), or group of organisms.

In some embodiments, the present disclosure provides homozygotes. As used herein, the term "homozygote" refers to an individual cell or plant having the same alleles at one or more loci.

In some embodiments, the present disclosure provides homozygous plants. As used herein, the term "homozygous" refers to the presence of identical alleles at one or more loci in homologous chromosomal segments.

In some embodiments, the present disclosure provides hemizygotes. As used herein, the term "hemizygotes" or "hemizygous" refers to a cell, tissue, organism or plant in which a gene is present only once in a genotype, as a gene in a haploid cell or organism, a sex-linked gene in the heterogametic sex, or a gene in a segment of chromosome in a diploid cell or organism where its partner segment has been deleted.

In some embodiments, the present disclosure provides heterozygotes. As used herein, the terms "heterozygote" and "heterozygous" refer to a diploid or polyploid individual cell or plant having different alleles (forms of a given gene) present at least at one locus. In some embodiments, the cell or organism is heterozygous for the gene of interest that is under control of the synthetic regulatory element.

The disclosure provides self-pollination populations. As used herein, the term "self-crossing", "self-pollinated" or "self-pollination", "self-fertilized" or "self-fertilization" means the pollen of one flower on one plant is applied (artificially or naturally) to the ovule (stigma) of the same or a different flower on the same plant. In some embodiments, plants of the present disclosure are genetically stable, such that pollination between plants of the same cultivar produces offspring are still considered part of the same cultivar.

In some embodiments, the present disclosure teaches *Cannabis* plants, which are an annual, dioecious, flowering herb. Its leaves are typically palmately compound or digitate, with serrated leaflets. *Cannabis* normally has imperfect flowers, with staminate "male" and pistillate "female" flowers occurring on separate plants. It is not unusual, however, for individual plants of some *Cannabis* varieties to separately bear both male and female flowers (i.e., have monoecious plants). Although monoecious plants are often referred to as "hermaphrodites," true hermaphrodites (which are less common in *Cannabis*) bear staminate and pistillate structures on individual flowers, whereas monoecious plants bear male and female flowers at different locations on the same plant. In some embodiments, plants of the 'KIRSCHE' variety have been feminized, and only produce female inflorescences. In some embodiments, seeds of the 'KIRSCHE' variety produce plants that are greater than 99%, 98%, 97%, 96%, 95%, 94%, 93%, 92%, 91%, or 90% female.

Persons having skill in the art will be familiar with ways of inducing male flowers in otherwise female plants, including rodelization or colloidal silver treatments. Briefly, rodelization is the process of stressing female plants to induce pollen sac formations. This can be done by allowing unfertilized female flowers to go beyond harvest maturity in flowering conditions, which will trigger the formation of pollen sacs in the plant's last effort to self-fertilize before the end of the life cycle. Another way of triggering the formation pollen in otherwise feminized plants is to spray the feminized plants at the flowering stage with colloidal silver solutions (e.g. >30 ppm). After several sprays, the plants will start forming pollen sacks. Other forms of silver, such as silver nitrate and silver thiosulfate are also effective. Also, hormones such as gibberellins can be used to induce male flowers on female *Cannabis* plants. Additional methods of inducing male flowers have been known to one of ordinary skill in the art, e.g., methods discussed in Ram and Sett (Theoretical and Applied Genetics, 1982, 62(4):369-375) and methods discussed in Ram and Jaiswal (Plant, 1972, 105(3):263-266), each of which is incorporated by reference in its entirety for all purposes.

As used herein, a "dioecious" plant refers to a plant having either only male flowers (androecious) or female flowers (gynoecious).

As used herein, a "monoecious" plant is a plant having both male and female or bisexual flowers, or both female and male or bisexual flowers. Plants bearing separate flowers of both sexes at the same time are called simultaneously or synchronously monoecious. Plants bearing flowers of one sex at one time are called consecutively monoecious.

The disclosure provides ovules and pollens of plants. As used herein when discussing plants, the term "ovule" refers to the female gametophyte, whereas the term "pollen" means the male gametophyte.

The disclosure provides methods for obtaining plants comprising recombinant genes through transformation. As used herein, the term "transformation" refers to the transfer of nucleic acid (i.e., a nucleotide polymer) into a cell. As used herein, the term "genetic transformation" refers to the transfer and incorporation of DNA, especially recombinant DNA, into a cell.

The disclosure provides transformants comprising recombinant genes. As used herein, the term "transformant" refers to a cell, tissue or organism that has undergone transformation. The original transformant is designated as "T0." Selfing the T0 produces a first transformed generation designated as "$F_1$" or "$T_1$."

In some embodiments, the present disclosure refers to inflorescences from a *Cannabis* plant comprising particular cannabinoid and terpene contents (i.e., inflorescences comprising no more than 0.3% THC). In some embodiments, inflorescences, such as dried inflorescences, described as having cannabinoid content are female inflorescences. In some embodiments, the inflorescences are grown "sinsemilla," in the absence of male plants to avoid pollination. Thus in some embodiments, the female inflorescences of the present disclosure are seedless, and in many cases, un-pollinated. The term "inflorescence" and "flower" are used interchangeably throughout this document.

Unless otherwise noted, references to cannabinoids in a plant, plant part, extract, or composition of the present disclosure should be understood as references to both the acidic and decarboxylated versions of the compound (e.g., potential THC as determined by the conversion guidelines described in this document, and understood by those skilled in the art). For example, unless otherwise stated or clear from the context, references to high CBD contents of a *Cannabis* plant in this disclosure should be understood as references to the combined CBD and CBDA content (accounting for weight loss during decarboxylation).

Detailed Botanical Description

The present disclosure relates to a new and distinct hemp (*Cannabis sativa* L.) cultivar designated as 'KIRSCHE.' Whole-plant hemp extracts from 'KIRSCHE' contain an assortment of phytocannabinoids (e.g., CBD), terpenes, flavonoids and other minor but valuable hemp compounds that work synergistically to heighten effects of products produced from 'KIRSCHE.' This synergistic effect is sometimes referred to as the "entourage effect." 'KIRSCHE' extracts can be used to produce a variety of products, including liquid and capsule forms for oral administration, topical products, cosmetic products, infused beverages, sport products and hemp-infused pet treats.

Despite *Cannabis* being consumed since at least the third millennium BC, complete scientific corroboration for uses of CBD are still in their infancy. Industry reports suggest CBD is used for a variety of health and wellness purposes, including as a sleep aid, coping with daily stress, fighting anxiety, relieving pain, assisting with cognitive function and boosting immune health. Significant research is currently being conducted at a variety of laboratories on the use of CBD as it relates to epilepsy, Post-Traumatic Stress Disorder (PTSD), cancer, autism, neuroprotection, anti-inflammatory effects, anti-tumor effects and anti-psychotic effects.

'KIRSCHE' is a selection resulting from a series of controlled-crosses using hemp germplasm(s). Specifically, 'KIRSCHE' is a hybrid maintained by crossing two parents maintained at applicant's facilities. The primary goal of the breeding program was to develop a new hemp variety with improved disease resistance, as well as high cannabidiolic acid (CBDA) concentrations and low tetrahydrocannabinolic acid (THCA) concentrations in its mature female flowers.

KIRSCHE' has not been observed under all possible environmental conditions, and the phenotype may vary significantly with variations in environment. The following observations, measurements, and comparisons describe this plant as grown in the field in Colorado.

Plants for the botanical measurements in the present application are annual plants. In the following description, the color determination is in accordance with The Royal Horticultural Society Colour Chart, Sixth Edition (2015), except where general color terms of ordinary dictionary significance are used.

Tables 1-5, below, provide the morphological and physiological characteristics of the 'KIRSCHE' variety as measured on Sep. 17, 2019. Morphological and physiological characteristics of 'LINDOREA' gathered in the same location and on the same date are provided for comparative purposes.

TABLE 1

General Characteristics

| Characteristics | New Variety ('KIRSCHE') | Check Variety ('LINDOREA') |
| --- | --- | --- |
| Plant life forms | An herbaceous plant (herb). | An herbaceous plant (herb). |
| Plant origin | First generation cross (hybrid) between two lines maintained at applicant's facilities. | First generation cross (hybrid) between two lines maintained at applicant's facilities. |
| Plant propagation | Maintained through seed by crossing parental lines to generate new hybrid seed. | Maintained through seed by crossing parental lines to generate new hybrid seed. |
| Propagation ease | Easy. | Easy. |
| Propagation condition | Place seeds in soil. | Place seeds in soil. |
| Height (Unit: meters) | 1.75 m-2.11 m. | 1.6 m-1.99 m. |
| Width (Unit: meters) | 0.94 m-1.57 m. | 0.89 m-1.5 m. |
| Resistance to pests or diseases | *Pseudomonas* spp., *Septoria* spp., *Cercospora* spp., *Bipolaris* spp., and possibly *Botrytis* spp. and *Sclerotinia* spp. | *Pseudomonas* spp., *Septoria* spp., *Cercospora* spp., *Bipolaris* spp., and possibly *Botrytis* spp. and *Sclerotinia* spp. More overall disease resistance than 'Kirsche'. |
| Genetically-modified organism | No. | No. |

TABLE 2

Leaf/Foliage

| Characteristics | New Variety ('KIRSCHE') | Check Variety ('LINDOREA') |
| --- | --- | --- |
| Leaf arrangement | Floral structures seem to be alternate, but changes to that about midway through growth from opposite (where subsequent branch points rotated 90-degrees until alternation began). Alternate leaves have varying degrees of internode distance. | Floral structures seem to be alternate, but changes to that about midway through growth from opposite (where subsequent branch points rotated 90-degrees until alternation began). Alternate leaves have varying degrees of internode distance. |
| Leaf shape | Palmately compound | Palmately compound. |
| Leaf structure | Serrated margins. Leaflets gladiate to somewhat linear with the tip tapering to an acute to acuminate apex, with the widest point halfway to above the leaflet midpoint. | Lightly serrated margins. Leaflets gladiate to linear with the tip tapering to acute to acuminate apex. A characteristic and distinctive curve/bend at leaflet apex. Leaflets are widely |

TABLE 2-continued

| Leaf/Foliage | | |
|---|---|---|
| Characteristics | New Variety ('KIRSCHE') | Check Variety ('LINDOREA') |
| Leaf margins | Serrated, with the basal/outward side of the tip convex and the inner/top side of the tip slightly concave. Teeth are pointed toward the leaflet apex. Sometimes teeth tips raise up above the leaf plane. | spaced, 30-40 degrees. Widest point on average about midway, but can be above or below. Serrated, with the basal/outward side of the tip slightly convex and the inner/top side of the tip slightly concave. Teeth are pointed toward the leaflet apex. Sometimes teeth tips raise up above the leaf plane. Top/inner margins less deeply notched and flatter than 'Kirsche'. |
| Leaf hairs | Bottom surface of mature leaves are strigillose to canescent. Visible to the naked eye, but give the surface a whiter color and slightly reflective or iridescent sheen. Top surfaces of mature leaves are smooth but dotted with stalk-less glandular trichomes, some bearing hooks especially along leaf margins. | Bottom surface of mature leaves are strigillose to canescent. Visible to the naked eye, but give the surface a whiter color and slightly reflective or iridescent sheen. Top surfaces of mature leaves are smooth but dotted with non-glandular (spikey) and stalk-less glandular trichomes, some bearing hooks especially along leaf margins. |
| Leaf hair Location | Randomly to evenly spread across the surface, as described above. | Randomly to evenly spread across the surface, as described above. |
| Leaf length with petiole at maturity (Unit: centimeters) | 4.45 cm- 20.95 cm. | 15.24 cm-20.95 cm. |
| Petiole length at maturity (Unit: centimeters) | 0.5 cm-6.4 cm. | 3.3 cm-7.9 cm. |
| Petiole color (RHS No.) | 146A-B, 144B-C, 145A-B, 143C, 146C-D. | 145A-B, 144A-C, 146C-D, 143C. |
| Anthocyanin color and intensity in Petioles | Can occur, especially in senescence. Moderate-red purple lines. Not solid, infrequent. | Mostly absent. |
| Stipule length at maturity (Unit: millimeters) | 4 mm-12 mm. | 6 mm-13 mm. |
| Stipule color (RHS No.) | 149B, 144C, 146C, 145A-B, N148A-B. | Same as young stem (almost all senesced at maturity); 141C, 143C, 144B-C, 145C-D before dying off. |
| Stipule shape | A non-rigid, spine-like leaf structure. With white, paper-like edges. Wider at the base, tapering to the apex. Can become curled to form a tube. Often absent on mature leaves due to senescence. | A non-rigid, spine-like leaf structure. With white, paper-like edges. Wider at the base (and wider than 'Kirsche'), tapering to the a thin-point apex. Can become curled to form a tube. Often absent on mature leaves due to senescence (almost all senesced at maturity). More difficult to find than in 'Kirsche', but overall larger. |
| No. of leaflets | 3-7. Mostly 7. | 3-7 with 5 being the most prominent. |
| Middle largest (longest) leaflet length (Unit: centimeters) | 2.54 cm-15.24 cm. | 10.79 cm-13.97 cm. |
| Middle largest (longest) leaflet width (Unit: centimeters) | 0.5 cm-2.1 cm. | 1.2 cm-1.6 cm |
| No. teeth of middle leaflet | 19-34. | 21-40 |

TABLE 2-continued

Leaf/Foliage

| Characteristics | New Variety ('KIRSCHE') | Check Variety ('LINDOREA') |
|---|---|---|
| Leaf (upper side-adaxial) color (RHS No.) | NN137A-B, 137A-B, 146A, 147A. | 137A-B, NN137A-B, 144A, 146A |
| Leaf (lower side-abaxial) color (RHS No.) | 147B, 148B, 137B, N148A, 146A, maybe 191A. | Most exhibit 146A-B. Others range between 147B, 148B, N148A, 137C, and 144A. |
| Leaf glossiness | No. | No. |
| Vein/midrib shape | Midvein is straight down the middle of each leaflet (percurrent). Secondary venation branches off the main vein in a slightly alternate pattern and goes all the way to the tooth edge without connecting to other veins. On the top side of the leaf, veins look slightly recessed, but on the bottom veins protrude off the surface. | Midvein is straight down the middle of each leaflet (percurrent). Secondary venation branches off the main vein in a slightly alternate pattern and goes all the way to the tooth edge without connecting to other veins. On the top side of the leaf, veins look slightly recessed, but on the bottom veins protrude off the surface. |
| Vein/midrib color (RHS No.) | Most like 147C and N148C. Others exhibit range from 148B-D, N147C, 146B. | N148A-D, 147C, 145A-C, 148B-D |

TABLE 3

Stem

| Characteristics | New Variety ('KIRSCHE') | Check Variety ('LINDOREA') |
|---|---|---|
| Stem shape | Generally round with broad ribs running parallel to the stem causing shallow furrows. Where side branches meet the main stem in the most mature sections, a bulging on the main stem typically on the sides is noticeable. In the most mature parts of the stem or in wounds, a woody appearance is produced. At maturity, the base of the stem is the widest point. | Generally round with broad ribs running parallel to the stem causing very shallow furrows. Where side branches meet the main stem in the most mature sections, a bulging on the main stem typically on the sides is noticeable and has a squared appearance. In the most mature parts of the stem or in wounds, a woody appearance is produced. At maturity, the base of the stem is the widest point. Side branches are more slender than 'Kirsche'. |
| Stem diameter at base (Unit: centimeters) | 3.9 cm-6.6 cm. | 2.9 cm-5.9 cm |
| Stem color (RHS No.) | Young (139C, 143A-C, 141C, 144A); mature woody (161A, 199C, 165B-C, 164B-C). | Young/green (143A-C, 144A-B, 146B); woody at base (161A-C, 162B-C) |
| Stem pith type | Mature branches tend to be hollow. If present, pith is thin. | Mostly solid with miniscule hollowness. Thin to medium. Largely dependent on age. |
| Depth of Main Stem Grooves | Shallow to medium. | Shallow. |
| Internode length (Unit: centimeters) | 1.4 cm-12.3 cm. | 1.8-10.1 cm |

TABLE 4

Inflorescence (Female/Pistillate Flowers)

| Characteristics | New Variety ('KIRSCHE') | Check Variety ('LINDOREA') |
|---|---|---|
| Flowering (blooming) habit | 'Kirsche' flowers a few weeks later than 'Lindorea' and has lower yields with smaller inflorescences. 'Kirsche' inflorescences are more | Flowers a few weeks earlier than 'Kirsche' in maturity and has higher yields with larger inflorescences. |

TABLE 4-continued

| Characteristics | New Variety ('KIRSCHE') | Check Variety ('LINDOREA') |
|---|---|---|
| | cylinder-like and less tapered. | Inflorescences are more bulky and tapered as if a wide inverted cone. |
| Proportion of female plants | >99%. Less than 1% of the observed plants produce male flowers or exhibit monoecious (female/male) tendencies. | >99%. Less than 1% of the observed plants produce male flowers or exhibit monoecious (female/male) tendencies. |
| Inflorescence position | Generally above, however leaves to emerge along nodal points throughout the inflorescence (leaflets). | Generally above, however leaves to emerge along nodal points throughout the inflorescence (leaflets). |
| Flower arrangement | Cymose. | Cymose |
| Flower (compound cyme) diameter (Unit: centimeters) | 1.91 cm-17.78 cm. | 2.54 cm-10.16 cm. |
| Bract shape | Photosynthetic, heavily trichomated. Round base with beaked tip where stigmas emerge from. Slightly ovoid. | Photosynthetic, heavily trichomated. Slightly rounded base with beaked tip where stigmas emerge from. More linear and pointed (less ovoid) than 'Kirsche'. |
| Bract length (Unit: millimeters) | 2 mm-6 mm. | 2-7 mm |
| Bract color (RHS No.) | Most exhibit NN137, N137B-C. Others exhibit range including 137A-D, 138A, 139C, 141C, 143A-C, and 146A-B. | 145A-B, 144B-C, 143A, 137C-D, 146B, 147A-B |
| Stigma shape | Highly influenced by environment (abundance of pollen). Slender, slightly wider at the base (slenderly tapering) with pointed tip. Covered in minute papillae. | Highly influenced by environment (abundance of pollen). Slender, slightly wider at the base (slenderly tapering) with pointed tip. Covered in minute papillae. |
| Stigma length (Unit: millimeters) | 3 mm-9 mm. | 3-10 mm |
| Stigma color (RHS No.) | Most exhibit 157A-D. Others show 190D, 196D, 149D, 195D, 193D,B,A, 130D, 192C (rusty lighter than 200D). Some individuals with white-only and white-blush stigmas. Of individuals with white and pink stigmas, 'Kirsche' has more of a speckled appearance. | 142D, 130D, 145D, 155A-C, NN155B&D, 157B-D; Rusty tips (199C, 199C-D); Light hints of blush (185B, 71B-C, 64B, 61C) Some individuals with white-only and white-blush stigmas. Of individuals with white and pink stigmas, 'Lindorea' has a sunset-like fade in the flower. |
| Trichome shape | Capitate and bulbous. Sessile, stalked, and non-glandular trichomes are all present. | Capitate and bulbous (with bulbs slightly bigger than 'Kirsche'). Sessile, stalked, and non-glandular trichomes are all present. Bulb size could be affected by maturity level/stage. |
| Trichome color (RHS No.) | Translucent to milky, some amber; N155A-D; Translucent-Clear-Milky. Can reflect blue from the sky or green from leaf Can also turn yellow-brown-amber, brownish-orange. | N155A-D; Translucent-Clear-Milky. Can reflect blue from the sky or green from leaf Can also turn yellow-brown-amber, brownish-orange. |
| Terminal bud color (RHS No.) | Most exhibit NN137 and N137B-C. Others exhibit 137A-D, 138A, 139C, 141C, 143A-C, 146A-B. | 145A-B, 144B-C, 143A, 137C-D, 146B, 147A-B |
| Pedicel shape | Absent. | Absent |
| Staminate shape | Absent. | Absent |
| Sepal shape | Absent. | Absent |
| Pollen description | Absent. | Absent |
| Seed description | Seed is mostly medium brown almost with a silvery-hue, some speckled, with an average 1000 count seed weight of 11-14 g. | 'Lindorea' seed is a medium to dark silver brown, some with stripes, with an average 1000 count seed weight of 10-12 g. |
| Petal shape | Absent. | Absent |

TABLE 5

| Other Characteristics | | |
| --- | --- | --- |
| Characteristics | New Variety ('KIRSCHE') | Check Variety ('LINDOREA') |
| Aroma | A sweet, musky floral scent with hints of cedar, sage, and eucalyptus. More pungent and cedar-like musky than 'Lindorea'. | Sweet floral with hints of bubble gum, melon, and citrus. A brighter, sweeter floral smell than 'Kirsche'. |
| Terpenes | Slightly more therapeutic terpene profile. See Table 7. | Slightly less therapeutic profile than 'KIRSCHE'. |
| Cannabinoids | About 0.24% to about 0.27% THC potential by dry weight of the inflorescence. About 8.77% to about 9.93% CBD potential by dry weight of the inflorescence. | About 0.2% to about 0.25% THC potential by dry weight of the inflorescence. About 7.23% to about 7.66% CBD potential by dry weight of the inflorescence. |

Table 6 includes detailed information of the hemp plant named 'KIRSCHE' for profiles of total CBD and THC concentrations as tested on six different flower samples. The claimed 'KIRSCHE' variety was tested by the third party service provider using High Performance Liquid Chromatography (HPLC). Table 7 includes detailed information of the terpene profile of the hemp plant named 'KIRSCHE' as measured by gas chromatography by a third party laboratory.

As used herein, the term "maturity," "harvest maturity," or "floral maturity" refers to the developmental stage at which the 'KIRSCHE' plant is harvested. Persons having skill in the art will recognize maturity based on the plant's morphologies. It is also good practice to conduct periodic cannabinoid content (i.e., potency) tests throughout the development of the plant to ensure that harvest occurs at maturity. 'KIRSCHE' is a photoperiod sensitive plant. Therefore, in some embodiments, time to maturity depends largely on the day/night cycles where grown. In Colorado as example, 'KIRSCHE' starts flowering 11-13 weeks after planting depending on planting date. 'KIRSCHE' starts flowering around late August 8/23-8/30 when it is planted in May/June.

In some embodiments, stigma color can also be an indication of maturity for 'KIRSCHE'. If all stigmas are red or browning it could indicate 'KIRSCHE' is past maturity. In some embodiments, one may harvest when some stigmas are still white.

Growing conditions throughout the plant's life cycle, nutrient variations, and environmental factors can all influence the amount of time for 'KIRSCHE' plants to reach harvest maturity. The present disclosure uses the terms "maturity," "harvest maturity," and "floral maturity" interchangeably. In some embodiments, harvest maturity can encompass any period after the emergence of inflorescences, but before the THC content of any inflorescence surpasses 0.3%.

In some instances, the botanical descriptions disclosed herein reflect the range of phenotypical variation observed under indoor and outdoor growth conditions. Total Potential THC/CBD contents presented in this document reflect the total potential (i.e., decarboxylated) THC and CBD content after decarboxylation of the THCA and CBDA contents of the sample. The formula used for this calculation is reproduced below for the Office's convenience. Total THC=THC+(THCA*(0.877)). Total CBD=CBD+(CBDA*(0.877)).

When 'KIRSCHE' is compared to the check variety ('LINDOREA'), 'KIRSCHE' and 'LINDOREA' were both bred primarily for disease resistance. 'KIRSCHE' was bred for disease resistance and has a more therapeutic terpene profile than 'LINDOREA.' 'KIRSCHE' shows less overall disease resistance than 'KIRSCHE', but 'KIRSCHE' still performs well. Common pathogens that 'KIRSCHE' and 'LINDOREA' are resistant/tolerant to include: *Pseudomonas* spp., *Septoria* spp., *Cercospora* spp., *Bipolaris* spp., and possibly *Botrytis* spp. and *Sclerotinia* spp.

'KIRSCHE' and 'LINDOREA' show good vigor, health, and uniformity. 'KIRSCHE' is a few weeks later than 'LINDOREA' in maturity and has lower yields with smaller inflorescences. 'LINDOREA' inflorescences are more bulky and tapered as if a wide inverted cone, and 'KIRSCHE' inflorescences are more cylinder-like and less tapered. 'KIRSCHE' and 'LINDOREA' have individuals with white-only and white-blush stigmas. Pink blush stigma coloration seems to be environmentally induced (certain fields had more pink). Of the individuals that have white and pink stigmas, while 'LINDOREA' has a sunset-like fade in the flower, 'KIRSCHE' has a more speckled appearance. While the aroma of 'LINDOREA' is sweeter and fruiter, that of 'KIRSCHE' is more cedar-like and musky.

*Cannabis* Hemp Breeding Methods

In some embodiments, the plants of the present disclosure can be used to produce new plant varieties. In some embodiments, the plants are used to develop new, unique and superior varieties or hybrids with desired phenotypes. As used herein, the term "plant breeding techniques" comprises all of the plant breeding techniques disclosed in this section of the application, and well known to persons having skill in the art. Thus, in some embodiments, plant breeding methods encompass the application of recurrent selection, mass selection, hybridization, open-pollination, backcrossing, pedigree breeding, marker assisted selection breeding, mutation breeding, gene editing, and combinations thereof.

In some embodiments, selection methods, e.g., molecular marker assisted selection, can be combined with breeding methods to accelerate the process. Additional breeding methods have been known to one of ordinary skill in the art, e.g., methods discussed in Chahal and Gosal (Principles and procedures of plant breeding: biotechnological and conventional approaches, CRC Press, 2002, ISBN 084931321X, 9780849313219), Taji et al. (In vitro plant breeding, Routledge, 2002, ISBN 156022908X, 9781560229087), Richards (Plant breeding systems, Taylor & Francis US, 1997, ISBN 0412574500, 9780412574504), Hayes (Methods of Plant Breeding, Publisher: READ BOOKS, 2007, ISBN1406737062, 9781406737066), each of which is incorporated by reference in its entirety for all purposes. The

*Cannabis* genome has been sequenced recently (van Bakel et al., The draft genome and transcriptome of *Cannabis sativa*, Genome Biology, 12(10):R102, 2011). Molecular markers for *Cannabis* plants are described in Datwyler et al. (Genetic variation in hemp and marijuana (*Cannabis sativa* L.) according to amplified fragment length polymorphisms, J Forensic Sci. 2006 March; 51(2):371-5.), Pinarkara et al., (RAPD analysis of seized marijuana (*Cannabis sativa* L.) in Turkey, Electronic Journal of Biotechnology, 12(1), 2009), Hakki et al., (Inter simple sequence repeats separate efficiently hemp from marijuana (*Cannabis sativa* L.), Electronic Journal of Biotechnology, 10(4), 2007), Datwyler et al., (Genetic Variation in Hemp and Marijuana (*Cannabis sativa* L.) According to Amplified Fragment Length Polymorphisms, J Forensic Sci, March 2006, 51(2):371-375), Gilmore et al. (Isolation of microsatellite markers in *Cannabis sativa* L. (marijuana), Molecular Ecology Notes, 3(1): 105-107, March 2003), Pacifico et al., (Genetics and marker-assisted selection of chemotype in *Cannabis sativa* L.), Molecular Breeding (2006) 17:257-268), and Mendoza et al., (Genetic individualization of *Cannabis sativa* by a short tandem repeat multiplex system, Anal Bioanal Chem (2009) 393:719-726), each of which is herein incorporated by reference in its entirety for all purposes.

In some embodiments, molecular markers are designed and made, based on the genome of the plants of the present application. In some embodiments, the molecular markers are selected from Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs). Amplified Fragment Length Polymorphisms (AFLPs), and Simple Sequence Repeats (SSRs) which are also referred to as Microsatellites, etc. Methods of developing molecular markers and their applications are described by Avise (Molecular markers, natural history, and evolution, Publisher: Sinauer Associates, 2004, ISBN 0878930418, 9780878930418), Srivastava et al. (Plant biotechnology and molecular markers, Publisher: Springer, 2004, ISBN1402019114, 9781402019111), and Vienne (Molecular markers in plant genetics and biotechnology, Publisher: Science Publishers, 2003), each of which is incorporated by reference in its entirety for all purposes.

The molecular markers can be used in molecular marker assisted breeding. For example, the molecular markers can be utilized to monitor the transfer of the genetic material. In some embodiments, the transferred genetic material is a gene of interest, such as genes that contribute to one or more favorable agronomic phenotypes when expressed in a plant cell, a plant part, or a plant.

Details of existing *Cannabis* plants varieties and breeding methods are described in Potter et al. (2011, World Wide Weed: Global Trends in *Cannabis* Cultivation and Its Control), Holland (2010, The Pot Book: A Complete Guide to *Cannabis*, Inner Traditions/Bear & Co, ISBN1594778981, 9781594778988), Green I (2009, The *Cannabis* Grow Bible: The Definitive Guide to Growing Marijuana for Recreational and Medical Use, Green Candy Press, 2009, ISBN 1931160589, 9781931160582), Green II (2005, The *Cannabis* Breeder's Bible: The Definitive Guide to Marijuana Genetics, *Cannabis* Botany and Creating Strains for the Seed Market, Green Candy Press, 1931160279, 9781931160278), Starks (1990, Marijuana Chemistry: Genetics, Processing & Potency, ISBN 0914171399, 9780914171393), Clarke (1981, Marijuana Botany, an Advanced Study: The Propagation and Breeding of Distinctive *Cannabis*, Ronin Publishing, ISBN 091417178X, 9780914171782), Short (2004, Cultivating Exceptional *Cannabis*: An Expert Breeder Shares His Secrets, ISBN 1936807122, 9781936807123), Cervantes (2004, Marijuana Horticulture: The Indoor/Outdoor Medical Grower's Bible, Van Patten Publishing, ISBN 187882323X, 9781878823236), Franck et al. (1990, Marijuana Grower's Guide, Red Eye Press, ISBN 0929349016, 9780929349015), Grotenhermen and Russo (2002, *Cannabis* and Cannabinoids: Pharmacology, Toxicology, and Therapeutic Potential, Psychology Press, ISBN 0789015080, 9780789015082), Rosenthal (2007, The Big Book of Buds: More Marijuana Varieties from the World's Great Seed Breeders, ISBN 1936807068, 9781936807062), Clarke, RC (*Cannabis*: Evolution and Ethnobotany 2013 (In press)), King, J (Cannabible Vols 1-3, 2001-2006), and four volumes of Rosenthal's Big Book of Buds series (2001, 2004, 2007, and 2011), each of which is herein incorporated by reference in its entirety for all purposes.

Classical breeding methods can be included in the present disclosure to introduce one or more recombinant expression cassettes of the present disclosure into other plant varieties, or other close-related species that are compatible to be crossed with the transgenic plant. In some embodiments, the recombinant expression cassette can encode for a desirable phenotype, including herbicide resistance, disease or pest resistance, insect resistance, resistance to antibiotics, or additional traits, as disclosed in this application.

In some embodiments, said method comprises (i) crossing any one of the plants of the present disclosure comprising the expression cassette as a donor to a recipient plant line to create a $F_1$ population; (ii) selecting offspring that have expression cassette. Optionally, the offspring can be further selected by testing the expression of the gene of interest. Thus in some embodiments, the present disclosure teaches crossing a transgenic plant with the presently disclosed 'KIRSCHE' plant.

In some embodiments, complete chromosomes of the donor plant are transferred. For example, the transgenic plant with the expression cassette can serve as a male or female parent in a cross pollination to produce offspring plants, wherein by receiving the transgene from the donor plant, the offspring plants have the expression cassette.

In a method for producing plants having the expression cassette, protoplast fusion can also be used for the transfer of the transgene from a donor plant to a recipient plant. Protoplast fusion is an induced or spontaneous union, such as a somatic hybridization, between two or more protoplasts (cells in which the cell walls are removed by enzymatic treatment) to produce a single bi- or multi-nucleate cell. The fused cell that may even be obtained with plant species that cannot be interbred in nature is tissue cultured into a hybrid plant exhibiting the desirable combination of traits. More specifically, a first protoplast can be obtained from a plant having the expression cassette. A second protoplast can be obtained from a second plant line, optionally from another plant species or variety, preferably from the same plant species or variety, that comprises commercially desirable characteristics, such as, but not limited to disease resistance, insect resistance, valuable grain characteristics (e.g., increased seed weight and/or seed size) etc. The protoplasts are then fused using traditional protoplast fusion procedures, which are known in the art to produce the cross.

Alternatively, embryo rescue may be employed in the transfer of the expression cassette from a donor plant to a recipient plant. Embryo rescue can be used as a procedure to isolate embryos from crosses wherein plants fail to produce viable seed. In this process, the fertilized ovary or immature seed of a plant is tissue cultured to create new plants (see Pierik, 1999, *In vitro culture of higher plants*, Springer, ISBN 079235267x, 9780792352679, which is incorporated herein by reference in its entirety).

In some embodiments, the recipient plant is an elite line having one or more certain desired traits. Examples of desired traits include but are not limited to those that result in increased biomass production, production of specific chemicals, increased seed production, improved plant material quality, increased seed oil content, etc. Additional examples of desired traits include pest resistance, vigor, development time (time to harvest), enhanced nutrient content, novel growth patterns, aromas or colors, salt, heat, drought and cold tolerance, and the like. Desired traits also include selectable marker genes (e.g., genes encoding herbicide or antibiotic resistance used only to facilitate detection or selection of transformed cells), hormone biosynthesis genes leading to the production of a plant hormone (e.g., auxins, gibberellins, cytokinins, abscisic acid and ethylene that are used only for selection), or reporter genes (e.g. luciferase, β-glucuronidase, chloramphenicol acetyl transferase (CAT, etc.). The recipient plant can also be a plant with preferred chemical compositions, e.g., compositions preferred for medical use or industrial applications.

Classical breeding methods can be used to produce new varieties of *Cannabis* according to the present disclosure. Newly developed $F_1$ hybrids can be reproduced via asexual reproduction.

Open-Pollinated Populations. The improvement of open-pollinated populations of such crops as *Cannabis*, rye, many maizes and sugar beets, herbage grasses, legumes such as alfalfa and clover, and tropical tree crops such as cacao, coconuts, oil palm and some rubber, depends essentially upon changing gene-frequencies towards fixation of favorable alleles while maintaining a high (but far from maximal) degree of heterozygosity. Uniformity in such populations is impossible and trueness-to-type in an open-pollinated variety is a statistical feature of the population as a whole, not a characteristic of individual plants. Thus, the heterogeneity of open-pollinated populations contrasts with the homogeneity (or virtually so) of inbred lines, clones and hybrids.

Population improvement methods fall naturally into two groups, those based on purely phenotypic selection, normally called mass selection, and those based on selection with progeny testing. Interpopulation improvement utilizes the concept of open breeding populations; allowing genes to flow from one population to another. Plants in one population (cultivar, strain, ecotype, or any germplasm source) are crossed either naturally (e.g., by wind) or by hand or by bees (commonly *Apis mellifera* L. or *Megachile rotundata* F.) with plants from other populations. Selection is applied to improve one (or sometimes both) population(s) by isolating plants with desirable traits from both sources.

There are basically two primary methods of open-pollinated population improvement. First, there is the situation in which a population is changed en masse by a chosen selection procedure. The outcome is an improved population that is indefinitely propagatable by random-mating within itself in isolation. Second, the synthetic variety attains the same end result as population improvement but is not itself propagatable as such; it has to be reconstructed from parental lines or clones. These plant breeding procedures for improving open-pollinated populations are well known to those skilled in the art and comprehensive reviews of breeding procedures routinely used for improving cross-pollinated plants are provided in numerous texts and articles, including: Allard, *Principles of Plant Breeding*, John Wiley & Sons, Inc. (1960); Simmonds, *Principles of Crop Improvement*, Longman Group Limited (1979); Hallauer and Miranda, *Quantitative Genetics in Maize Breeding*, Iowa State University Press (1981); and, Jensen, *Plant Breeding Methodology*, John Wiley & Sons, Inc. (1988).

Mass Selection. In mass selection, desirable individual plants are chosen, harvested, and the seed composited without progeny testing to produce the following generation. Since selection is based on the maternal parent only, and there is no control over pollination, mass selection amounts to a form of random mating with selection. As stated herein, the purpose of mass selection is to increase the proportion of superior genotypes in the population.

Mutation breeding is another method of introducing new traits into the hemp plants of the present disclosure. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g., cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil)), related compounds (8-ethoxy caffeine), antibiotics (streptonigrin), alkylating agents (sulfur mustards, nitrogen mustards, epoxides, ethyleneamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques. Details of mutation breeding can be found in Allard, *Principles of Plant Breeding*, John Wiley & Sons, Inc. (1960). In addition, mutations created in other hemp plants may be used to produce a backcross conversion of hemp plants having all phenotypes of the 'KIRSCHE' line while comprising the mutation obtained from the other hemp plants.

Additional methods include, but are not limited to, expression vectors introduced into plant tissues using a direct gene transfer method, such as microprojectile-mediated delivery, DNA injection, electroporation, and the like. Additionally, expression vectors are introduced into plant tissues by using either microprojectile-mediated delivery with a biolistic device or by using *Agrobacterium*-mediated transformation. Transformant plants obtained with the protoplasm of the subject hemp plants are intended to be within the scope of the embodiments of the application.

Synthetics. A synthetic variety is produced by crossing inter se a number of genotypes selected for good combining ability in all possible hybrid combinations, with subsequent maintenance of the variety by open pollination. Whether parents are (more or less inbred) seed-propagated lines, makes no difference in principle. Parents are selected on general combining ability, sometimes by test crosses or toperosses, more generally by polycrosses. Parental seed lines may be deliberately inbred (e.g. by selfing or sib crossing). However, even if the parents are not deliberately inbred, selection within lines during line maintenance will ensure that some inbreeding occurs. Clonal parents will, of course, remain unchanged and highly heterozygous.

Whether a synthetic can go straight from the parental seed production plot to the farmer or must first undergo one or two cycles of multiplication depends on seed production and the scale of demand for seed.

While mass selection is sometimes used, progeny testing is generally preferred for polycrosses, because of their operational simplicity and obvious relevance to the objective, namely exploitation of general combining ability in a synthetic.

The numbers of parental lines or clones that enter a synthetic vary widely. In practice, numbers of parental lines range from 10 to several hundred, with 100-200 being the average. Broad based synthetics formed from 100 or more clones would be expected to be more stable during seed multiplication than narrow based synthetics.

Pedigreed varieties. A pedigreed variety is a superior genotype developed from selection of individual plants out of a segregating population followed by propagation and seed increase of self-pollinated offspring and careful testing of the genotype over several generations. This is an open pollinated method that works well with naturally self-pollinating species. This method can be used in combination with mass selection in variety development. Variations in pedigree and mass selection in combination are the most common methods for generating varieties in self-pollinated crops.

Hybrids. A hybrid is an individual plant resulting from a cross between parents of differing genotypes. Commercial hybrids are now used extensively in many crops, including corn (maize), sorghum, sugar beet, sunflower and broccoli. Hybrids can be formed in a number of different ways, including by crossing two parents directly (single cross hybrids), by crossing a single cross hybrid with another parent (three-way or triple cross hybrids), or by crossing two different hybrids (four-way or double cross hybrids).

Strictly speaking, most individuals in an out breeding (i.e., open-pollinated) population are hybrids, but the term is usually reserved for cases in which the parents are individuals whose genomes are sufficiently distinct for them to be recognized as different species or subspecies. Hybrids may be fertile or sterile depending on qualitative and/or quantitative differences in the genomes of the two parents. Heterosis, or hybrid vigor, is usually associated with increased heterozygosity that results in increased vigor of growth, survival, and fertility of hybrids as compared with the parental lines that were used to form the hybrid. Maximum heterosis is usually achieved by crossing two genetically different, highly inbred lines.

Targeting Induced Local Lesions in Genomes (TILLING). Breeding schemes of the present disclosure can include crosses with TILLING® plant lines. TILLING® is a method in molecular biology that allows directed identification of mutations in a specific gene. TILLING® was introduced in 2000, using the model plant *Arabidopsis thaliana*. TILLING® has since been used as a reverse genetics method in other organisms such as zebrafish, corn, wheat, rice, soybean, tomato and lettuce. The method combines a standard and efficient technique of mutagenesis with a chemical mutagen (e.g., Ethyl methanesulfonate (EMS)) with a sensitive DNA screening-technique that identifies single base mutations (also called point mutations) in a target gene. EcoTILLING is a method that uses TILLING® techniques to look for natural mutations in individuals, usually for population genetics analysis (see Comai, et al., 2003 The Plant Journal 37, 778-786; Gilchrist et al. 2006 Mol. Ecol. 15, 1367-1378; Mejlhede et al. 2006 Plant Breeding 125, 461-467; Nieto et al. 2007 BMC Plant Biology 7, 34-42, each of which is incorporated by reference hereby for all purposes). DEcoTILLING is a modification of TILLING® and EcoTILLING which uses an inexpensive method to identify fragments (Garvin et al., 2007, DEcoTILLING: An inexpensive method for SNP discovery that reduces ascertainment bias. Molecular Ecology Notes 7, 735-746). More detailed description on methods and compositions on TILLING® can be found in U.S. Pat. No. 5,994,075, US 2004/0053236 A1, WO 2005/055704, and WO 2005/048692, each of which is hereby incorporated by reference for all purposes.

In some embodiments, TILLING® can also be utilized for plants of the *Cannabis* genus including hemp plants. Thus in some embodiments, the breeding methods of the present disclosure include breeding with one or more TILLING plant lines with one or more identified mutations.

Gene editing technologies. Breeding and selection schemes of the present disclosure can include crosses with plant lines that have undergone genome editing. In some embodiments, the breeding and selection methods of the present disclosure are compatible with plants that have been modified using any gene and/or genome editing tool, including, but not limited to: ZFNs, TALENS, CRISPR, and Mega nuclease technologies. In some embodiments, persons having skill in the art will recognize that the breeding methods of the present disclosure are compatible with many other gene editing technologies. In some embodiments, the present disclosure teaches gene-editing technologies can be applied for a single locus conversion, for example, conferring hemp plant with herbicide resistance. In some embodiments, the present disclosure teaches that the single locus conversion is an artificially mutated gene or nucleotide sequence that has been modified through the use of breeding techniques taught herein.

In some embodiments, the breeding and selection methods of the present disclosure are compatible with plants that have been modified through Zinc Finger Nucleases. Three variants of the ZFN technology are recognized in plant breeding (with applications ranging from producing single mutations or short deletions/insertions in the case of ZFN-1 and -2 techniques up to targeted introduction of new genes in the case of the ZFN-3 technique); 1) ZFN-1: Genes encoding ZFNs are delivered to plant cells without a repair template. The ZFNs bind to the plant DNA and generate site specific double-strand breaks (DSBs). The natural DNA-repair process (which occurs through nonhomologous end-joining, NHEJ) leads to site specific mutations, in one or only a few base pairs, or to short deletions or insertions; 2) ZFN-2: Genes encoding ZFNs are delivered to plant cells along with a repair template homologous to the targeted area, spanning a few kilo base pairs. The ZFNs bind to the plant DNA and generate site-specific DSBs. Natural gene repair mechanisms generate site-specific point mutations e.g. changes to one or a few base pairs through homologous recombination and the copying of the repair template; and 3) ZFN-3: Genes encoding ZFNs are delivered to plant cells along with a stretch of DNA which can be several kilo base pairs long and the ends of which are homologous to the DNA sequences flanking the cleavage site. As a result, the DNA stretch is inserted into the plant genome in a site-specific manner.

In some embodiments, the breeding and selection methods of the present disclosure are compatible with plants that have been modified through Transcription activator-like (TAL) effector nucleases (TALENs). TALENS are polypeptides with repeat polypeptide arms capable of recognizing and binding to specific nucleic acid regions. By engineering the polypeptide arms to recognize selected target sequences, the TAL nucleases can be used to direct double stranded DNA breaks to specific genomic regions. These breaks can then be repaired via recombination to edit, delete, insert, or otherwise modify the DNA of a host organism. In some embodiments, TALENSs are used alone for gene editing (e.g., for the deletion or disruption of a gene). In other embodiments, TALs are used in conjunction with donor sequences and/or other recombination factor proteins that will assist in the Non-homologous end joining (NHEJ) process to replace the targeted DNA region. For more information on the TAL-mediated gene editing compositions and methods of the present disclosure, see U.S. Pat. Nos. 8,440,432; 8,450,471; 8,586,526; 8,586,363; 8,592,645; 8,697,853; 8,704,041; 8,921,112; and 8,912,138, each of which is hereby incorporated in its entirety for all purposes.

In some embodiments, the breeding and selection methods of the present disclosure are compatible with plants that have been modified through Clustered Regularly Interspaced Short Palindromic Repeats (CRISPR) or CRISPR-associated (Cas) gene editing tools. CRISPR proteins were originally discovered as bacterial adaptive immunity systems which protected bacteria against viral and plasmid invasion. There are at least three main CRISPR system types (Type I, II, and III) and at least 10 distinct subtypes (Makarova, K. S., et.al., Nat Rev Microbiol. 2011 May 9; 9(6):467-477). Type I and III systems use Cas protein complexes and short guide polynucleotide sequences to target selected DNA regions. Type II systems rely on a single protein (e.g. Cas9) and the targeting guide polynucleotide, where a portion of the 5' end of a guide sequence is complementary to a target nucleic acid. For more information on the CRISPR gene editing compositions and methods of the present disclosure, see U.S. Pat. Nos. 8,697,359; 8,889,418; 8,771,945; and 8,871,445, each of which is hereby incorporated in its entirety for all purposes.

In some embodiments, the breeding and selection methods of the present disclosure are compatible with plants that have been modified through meganucleases. In some embodiments, meganucleases are engineered endonucleases capable of targeting selected DNA sequences and inducing DNA breaks. In some embodiments, new meganucleases targeting specific regions are developed through recombinant techniques which combine the DNA binding motifs from various other identified nucleases. In other embodiments, new meganucleases are created through semi-rational mutational analysis, which attempts to modify the structure of existing binding domains to obtain specificity for additional sequences. For more information on the use of meganucleases for genome editing, see Silva et al., 2011 Current Gene Therapy 11 pg 11-27; and Stoddard et al., 2014 Mobile DNA 5 pg 7, each of which is hereby incorporated in its entirety for all purposes.

Plant Transformation

Hemp plants of the present disclosure, such as 'KIRSCHE' can be further modified by introducing one or more transgenes which when expressed lead to desired phenotypes. The most common method for the introduction of new genetic material into a plant genome involves the use of living cells of the bacterial pathogen *Agrobacterium tumefaciens* to literally inject a piece of DNA, called transfer or T-DNA, into individual plant cells (usually following wounding of the tissue) where it is targeted to the plant nucleus for chromosomal integration. There are numerous patents governing *Agrobacterium* mediated transformation and particular DNA delivery plasmids designed specifically for use with *Agrobacterium*—for example, U.S. Pat. No. 4,536,475, EP0265556, EP0270822, WO8504899, WO8603516, U.S. Pat. No. 5,591,616, EP0604662, EP0672752, WO8603776, WO9209696, WO9419930, WO9967357, U.S. Pat. No. 4,399,216, WO8303259, U.S. Pat. No. 5,731,179, EP068730, WO9516031, U.S. Pat. Nos. 5,693,512, 6,051,757 and EP904362A1. *Agrobacterium*-mediated plant transformation involves as a first step the placement of DNA fragments cloned on plasmids into living *Agrobacterium* cells, which are then subsequently used for transformation into individual plant cells. *Agrobacterium*-mediated plant transformation is thus an indirect plant transformation method. Methods of *Agrobacterium*-mediated plant transformation that involve using vectors with no T-DNA are also well known to those skilled in the art and can have applicability in the present disclosure. See, for example, U.S. Pat. No. 7,250,554, which utilizes P-DNA instead of T-DNA in the transformation vector.

Direct plant transformation methods using DNA have also been reported. The first of these to be reported historically is electroporation, which utilizes an electrical current applied to a solution containing plant cells (M. E. Fromm et al., Nature, 319, 791 (1986); H. Jones et al., Plant Mol. Biol., 13, 501 (1989) and H. Yang et al., Plant Cell Reports, 7, 421 (1988). Another direct method, called "biolistic bombardment", uses ultrafine particles, usually tungsten or gold, that are coated with DNA and then sprayed onto the surface of a plant tissue with sufficient force to cause the particles to penetrate plant cells, including the thick cell wall, membrane and nuclear envelope, but without killing at least some of them (U.S. Pat. Nos. 5,204,253, 5,015,580). A third direct method uses fibrous forms of metal or ceramic consisting of sharp, porous or hollow needle-like projections that literally impale the cells, and also the nuclear envelope of cells. Both silicon carbide and aluminum borate whiskers have been used for plant transformation (Mizuno et al., 2004; Petolino et al., 2000; U.S. Pat. No. 5,302,523 US Application 20040197909) and also for bacterial and animal transformation (Kaepler et al., 1992; Raloff, 1990; Wang, 1995). There are other methods reported, and undoubtedly, additional methods will be developed. However, the efficiencies of each of these indirect or direct methods in introducing foreign DNA into plant cells are invariably extremely low, making it necessary to use some method for selection of only those cells that have been transformed, and further, allowing growth and regeneration into plants of only those cells that have been transformed.

For efficient plant transformation, a selection method must be employed such that whole plants are regenerated from a single transformed cell and every cell of the transformed plant carries the DNA of interest. These methods can employ positive selection, whereby a foreign gene is supplied to a plant cell that allows it to utilize a substrate present in the medium that it otherwise could not use, such as mannose or xylose (for example, refer U.S. Pat. Nos. 5,767,378; 5,994,629). More typically, however, negative selection is used because it is more efficient, utilizing selective agents such as herbicides or antibiotics that either kill or inhibit the growth of nontransformed plant cells and reducing the possibility of chimeras. Resistance genes that are effective against negative selective agents are provided on the introduced foreign DNA used for the plant transformation. For example, one of the most popular selective agents used is the antibiotic kanamycin, together with the resistance gene neomycin phosphotransferase (nptII), which confers resistance to kanamycin and related antibiotics (see, for example, Messing & Vierra, Gene 19: 259-268 (1982); Bevan et al., Nature 304:184-187 (1983)). However, many different antibiotics and antibiotic resistance genes can be used for transformation purposes (refer U.S. Pat. Nos. 5,034,322, 6,174,724 and 6,255,560). In addition, several herbicides and herbicide resistance genes have been used for transformation purposes, including the bar gene, which confers resistance to the herbicide phosphinothricin (White et al., *Nucl Acids Res* 18: 1062 (1990), Spencer et al., *Theor Appl Genet* 79: 625-631 (1990), U.S. Pat. Nos. 4,795,855, 5,378, 824 and 6,107,549). In addition, the dhfr gene, which confers resistance to the anticancer agent methotrexate, has been used for selection (Bourouis et al., *EMBO J.* 2(7): 1099-1104 (1983).

Genes can be introduced in a site directed fashion using homologous recombination. Homologous recombination permits site specific modifications in endogenous genes and thus inherited or acquired mutations may be corrected, and/or novel alterations may be engineered into the genome. Homologous recombination and site-directed integration in plants are discussed in, for example, U.S. Pat. Nos. 5,451, 513, 5,501,967 and 5,527,695.

Methods of producing transgenic plants are well known to those of ordinary skill in the art. Transgenic plants can now be produced by a variety of different transformation methods including, but not limited to, electroporation; microinjection; microprojectile bombardment, also known as particle acceleration or biolistic bombardment; viral-mediated transformation; and *Agrobacterium*-mediated transformation. See, for example, U.S. Pat. Nos. 5,405,765; 5,472,869; 5,538,877; 5,538,880; 5,550,318; 5,641,664; and 5,736,369; and International Patent Application Publication Nos. WO/2002/038779 and WO/2009/117555; Lu et al., (Plant Cell Reports, 2008, 27:273-278); Watson et al., Recombinant DNA, Scientific American Books (1992); Hinchee et al., Bio/Tech. 6:915-922 (1988); McCabe et al., Bio/Tech. 6:923-926 (1988); Toriyama et al., Bio/Tech. 6:1072-1074 (1988); Fromm et al., Bio/Tech. 8:833-839 (1990); Mullins et al., Bio/Tech. 8:833-839 (1990); Hiei et al., Plant Molecular Biology 35:205-218 (1997); Ishida et al., Nature Biotechnology 14:745-750 (1996); Zhang et al., Molecular Biotechnology 8:223-231 (1997); Ku et al., Nature Biotechnology 17:76-80 (1999); and, Raineri et al., Bio/Tech. 8:33-38 (1990)), each of which is expressly incorporated herein by reference in their entirety. Other references teaching the transformation of *Cannabis* plants and the production of callus tissue include Raharjo et al 2006, "Callus Induction and Phytochemical Characterization of *Cannabis sativa* Cell Suspension Cultures", Indo. J. Chem 6 (1) 70-74; and "The biotechnology of *Cannabis sativa*" by Sam R. Zwenger, electronically published April, 2009.

Microprojectile bombardment is also known as particle acceleration, biolistic bombardment, and the gene gun (Biolistic® Gene Gun). The gene gun is used to shoot pellets that are coated with genes (e.g., for desired traits) into plant seeds or plant tissues in order to get the plant cells to then express the new genes. The gene gun uses an actual explosive (.22 caliber blank) to propel the material. Compressed air or steam may also be used as the propellant. The Biolistic® Gene Gun was invented in 1983-1984 at Cornell University by John Sanford, Edward Wolf, and Nelson Allen. It and its registered trademark are now owned by E. I. du Pont de Nemours and Company. Most species of plants have been transformed using this method.

*Agrobacterium tumefaciens* is a naturally occurring bacterium that is capable of inserting its DNA (genetic information) into plants, resulting in a type of injury to the plant known as crown gall. Most species of plants can now be transformed using this method, including cucurbitaceous species. A transgenic plant formed using *Agrobacterium* transformation methods typically contains a single gene on one chromosome, although multiple copies are possible. Such transgenic plants can be referred to as being hemizygous for the added gene. A more accurate name for such a plant is an independent segregant, because each transformed plant represents a unique T-DNA integration event (U.S. Pat. No. 6,156,953). A transgene locus is generally characterized by the presence and/or absence of the transgene. A heterozygous genotype in which one allele corresponds to the absence of the transgene is also designated hemizygous (U.S. Pat. No. 6,008,437).

General transformation methods, and specific methods for transforming certain plant species (e.g., maize) are described in U.S. Pat. Nos. 4,940,838, 5,464,763, 5,149,645, 5,501, 967, 6,265,638, 4,693,976, 5,635,381, 5,731,179, 5,693,512, 6,162,965, 5,693,512, 5,981,840, 6,420,630, 6,919,494, 6,329,571, 6,215,051, 6,369,298, 5,169,770, 5,376,543, 5,416,011, 5,569,834, 5,824,877, 5,959,179, 5,563,055, and 5,968,830, each of which is incorporated herein by reference in its entirety for all purposes.

Non-limiting examples of methods for transforming *Cannabis* plants and *Cannabis* tissue culture methods are described in Zweger (The Biotechnology of *Cannabis sativa*, April 2009); MacKinnon (Genetic transformation of *Cannabis sativa* Linn: a multipurpose fiber crop, doctoral thesis, University of Dundee, Scotland, 2003), MacKinnon et al. (Progress towards transformation of fiber hemp, Scottish Crop Research, 2000), and US 20120311744, each of which is herein incorporated by reference in its entirety for all purposes. The transformation can be physical, chemical and/or biological.

Herbicide Resistance

Numerous herbicide resistance genes are known and may be employed with the invention. A non-limiting example is a gene conferring resistance to a herbicide that inhibits the growing point or meristem such as imidazolinone or sulfonylurea herbicides. As imidazolinone and sulfonylurea herbicides are acetolactate synthase (ALS)-inhibiting herbicides that prevent the formation of branched chain amino acids, exemplary genes in this category code for ALS and AHAS enzymes as described, for example, by Lee et al., *EMBO J.*, 7:1241, 1988; Gleen et al., *Plant Molec. Biology*, 18:1185, 1992; and Miki et al., *Theor. Appl. Genet.*, 80:449, 1990. As a non-limiting example, a gene may be employed to confer resistance to the exemplary sulfonylurea herbicide nicosulfuron.

Resistance genes for glyphosate (resistance conferred by mutant 5-enolpyruvylshikimate-3-phosphate synthase (EPSPS) and aroA genes, respectively) and other phosphono compounds such as glufosinate (phosphinothricin acetyltransferase (PAT) and *Streptomyces hygroscopicus* phosphinothricin acetyltransferase (bar) genes) may also be used. See, for example, U.S. Pat. No. 4,940,835 to Shah et al., which discloses the nucleotide sequence of a form of EPSPS that can confer glyphosate resistance. Non-limiting examples of EPSPS transformation events conferring glyphosate resistance are provided by U.S. Pat. Nos. 6,040,497 and 7,632,985. The MON89788 event disclosed in U.S. Pat. No. 7,632,985 in particular is beneficial in conferring glyphosate tolerance in combination with an increase in average yield relative to prior events.

A DNA molecule encoding a mutant aroA gene can be obtained under ATCC Accession No. 39256, and the nucleotide sequence of the mutant gene is disclosed in U.S. Pat. No. 4,769,061 to Comai. A hygromycin B phosphotransferase gene from *E. coli* that confers resistance to glyphosate in tobacco callus and plants is described in Penaloza-Vazquez et al., *Plant Cell Reports*, 14:482, 1995. European Patent Application Publication No. EP0333033 to Kumada et al., and U.S. Pat. No. 4,975,374 to Goodman et al., disclose nucleotide sequences of glutamine synthetase genes that confer resistance to herbicides such as L-phosphinothricin. The nucleotide sequence of a phosphinothricin acetyltransferase gene is provided in European Patent Application Publication No. EP0242246 to Leemans et al. DeGreef et al. (*Biotechnology*, 7:61, 1989) describe the production of transgenic plants that express chimeric bar genes coding for phosphinothricin acetyl transferase activity. Exemplary genes conferring resistance to a phenoxy class herbicide haloxyfop and a cyclohexanedione class herbicide sethoxydim are the Acct-S1, Acct-S2 and Acct-S3 genes described by Marshall et al., (*Theor. Appl. Genet.*, 83:435, 1992). As a non-limiting example, a gene may confer resistance to other exemplary phenoxy class herbicides that include, but are not limited to, quizalofop-p-ethyl and 2,4-dichlorophenoxyacetic acid (2,4-D).

Genes are also known that confer resistance to herbicides that inhibit photosynthesis such as, for example, triazine herbicides (psbA and gs+ genes) and benzonitrile herbicides (nitrilase gene). As a non-limiting example, a gene may confer resistance to the exemplary benzonitrile herbicide bromoxynil. Przibila et al. (*Plant Cell*, 3:169, 1991) describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al. (*Biochem. J.*, 285:173, 1992). 4-hydroxyphenylpyruvate dioxygenase (HPPD) is a target of the HPPD-inhibiting herbicides, which deplete plant plastoquinone and vitamin E pools. Rippert et al. (*Plant Physiol.*, 134:92, 2004) describes an HPPD-inhibitor resistant tobacco plant that was transformed with a yeast-derived prephenate dehydrogenase (PDH) gene. Protoporphyrinogen oxidase (PPO) is the target of the PPO-inhibitor class of herbicides; a PPO-inhibitor resistant PPO gene was recently identified in *Amaranthus tuberculatus* (Patzoldt et al., *PNAS*, 103(33):12329, 2006). The herbicide methyl viologen inhibits $CO_2$ assimilation. Foyer et al. (*Plant Physiol.*, 109:1047, 1995) describe a plant overexpressing glutathione reductase (GR) that is resistant to methyl viologen treatment. Siminszky (*Phytochemistry Reviews*, 5:445, 2006) describes plant cytochrome P450-mediated detoxification of multiple, chemically unrelated classes of herbicides. Modified bacterial genes have been successfully demonstrated to confer resistance to atrazine, a herbicide that binds to the plastoquinone-binding membrane protein $Q_B$ in photosystem II to inhibit electron transport. See, for example, studies by Cheung et al. (*PNAS*, 85:391, 1988), describing tobacco plants expressing the chloroplast psbA gene from an atrazine-resistant biotype of *Amaranthus hybridus* fused to the regulatory sequences of a nuclear gene, and Wang et al. (*Plant Biotech.* 1, 3:475, 2005), describing transgenic alfalfa, *Arabidopsis*, and tobacco plants expressing the atzA gene from *Pseudomonas* sp. that were able to detoxify atrazine.

Bayley et al. (*Theor. Appl. Genet.*, 83:645, 1992) describe the creation of 2,4-D-resistant transgenic tobacco and cotton plants using the 2,4-D monooxygenase gene tfdA from *Alcaligenes eutrophus* plasmid pJP5. U.S. Patent Application Publication No. 20030135879 describes the isolation of a gene for dicamba monooxygenase (DMO) from *Pseudomonas maltophilia* that is involved in the conversion of dicamba to a non-toxic 3,6-dichlorosalicylic acid and thus may be used for producing plants tolerant to this herbicide.

Other examples of herbicide resistance have been described, for instance, in U.S. Pat. Nos. 6,803,501; 6,448,476; 6,248,876; 6,225,114; 6,107,549; 5,866,775; 5,804,425; 5,633,435; 5,463,175.

Disease and Pest Resistance

Plant defenses are often activated by specific interaction between the product of a disease resistance gene (R) in the plant and the product of a corresponding avirulence (Avr) gene in the pathogen. A plant line can be transformed with a cloned resistance gene to engineer plants that are resistant to specific pathogen strains. See, for example Jones et al. (*Science*, 266:789-793, 1994) (cloning of the tomato Cf-9 gene for resistance to *Cladosporium flavum*); Martin et al. (*Science*, 262:1432-1436, 1993) (tomato Pto gene for resistance to *Pseudomonas syringae* pv. tomato); and Mindrinos et al. (*Cell*, 78(6):1089-1099, 1994) (*Arabidopsis* RPS2 gene for resistance to *Pseudomonas syringae*).

A viral-invasive protein or a complex toxin derived therefrom may also be used for viral disease resistance. For example, the accumulation of viral coat proteins in transformed plant cells imparts resistance to viral infection and/or disease development effected by the virus from which the coat protein gene is derived and related viruses. See Beachy et al. (*Ann. Rev. Phytopathol.*, 28:451, 1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus, and tobacco mosaic virus.

A virus-specific antibody may also be used. See, for example, Tavladoraki et al. (*Nature*, 366:469-472, 1993), who show that transgenic plants expressing recombinant antibody genes are protected from virus attack. Virus resistance has also been described in, for example, U.S. Pat. Nos. 6,617,496; 6,608,241; 6,015,940; 6,013,864; 5,850,023 and 5,304,730. Additional means of inducing whole-plant resistance to a pathogen include modulation of the systemic acquired resistance (SAR) or pathogenesis related (PR) genes, for example genes homologous to the *Arabidopsis thaliana* NIM1/NPR1/SAI1, and/or by increasing salicylic acid production (Ryals et al., *Plant Cell*, 8:1809-1819, 1996).

Logemann et al. (*Biotechnology*, 10:305-308, 1992), for example, disclose transgenic plants expressing a barley ribosome-inactivating gene that have an increased resistance to fungal disease. Plant defensins may be used to provide resistance to fungal pathogens (Thomma et al., *Planta*, 216:193-202, 2002). Other examples of fungal disease resistance are provided in U.S. Pat. Nos. 6,653,280; 6,573,361; 6,506,962; 6,316,407; 6,215,048; 5,516,671; 5,773,696; 6,121,436; and 6,316,407.

Nematode resistance has been described in, for example, U.S. Pat. No. 6,228,992, and bacterial disease resistance has been described in, for example, U.S. Pat. No. 5,516,671.

The use of the herbicide glyphosate for disease control in hemp plants containing event MON89788, which confers glyphosate tolerance, has also been described in U.S. Pat. No. 7,608,761.

Insect Resistance

One example of an insect resistance gene includes a *Bacillus thuringiensis* protein, a derivative thereof, or a synthetic polypeptide modeled thereon. See, for example, Geiser et al. (*Gene*, 48(1):109-118, 1986), who disclose the cloning and nucleotide sequence of a *Bacillus thuringiensis* δ-endotoxin gene. Moreover, DNA molecules encoding δ-endotoxin genes can be purchased from the American Type Culture Collection, Manassas, Va., for example, under ATCC Accession Nos. 40098, 67136, 31995 and 31998. Another example is a lectin. See, for example, Van Damme et al., (*Plant Molec. Biol.*, 24:825-830, 1994), who disclose the nucleotide sequences of several *Clivia miniata* mannose-binding lectin genes. A vitamin-binding protein may also be used, such as, for example, avidin. See PCT Application No. US93/06487, the contents of which are hereby incorporated by reference. This application teaches the use of avidin and avidin homologues as larvicides against insect pests.

Yet another insect resistance gene is an enzyme inhibitor, for example, protease, proteinase, or amylase inhibitors. See, for example, Abe et al. (*J. Biol. Chem.*, 262:16793-16797, 1987) describing the nucleotide sequence of a rice cysteine proteinase inhibitor; Linthorst et al. (*Plant Molec. Biol.*, 21:985-992, 1993) describing the nucleotide sequence of a cDNA encoding tobacco proteinase inhibitor I; and Sumitani et al. (*Biosci. Biotech. Biochem.*, 57:1243-1248, 1993) describing the nucleotide sequence of a *Streptomyces nitrosporeus* α-amylase inhibitor.

An insect-specific hormone or pheromone may also be used. See, for example, the disclosure by Hammock et al. (*Nature*, 344:458-461, 1990) of baculovirus expression of cloned juvenile hormone esterase, an inactivator of juvenile hormone; Gade and Goldsworthy (*Eds. Physiological System in Insects*, Elsevier Academic Press, Burlington, Mass., 2007), describing allostatins and their potential use in pest control; and Palli et al. (*Vitam. Horm.*, 73:59-100, 2005), disclosing use of ecdysteroid and ecdysteroid receptor in agriculture. The diuretic hormone receptor (DHR) was identified in Price et al. (*Insect Mol. Biol.*, 13:469-480, 2004) as another potential candidate target of insecticides.

Still other examples include an insect-specific antibody or an immunotoxin derived therefrom and a developmental-arrestive protein. See Taylor et al. (Seventh Int'l Symposium on Molecular Plant-Microbe Interactions, Edinburgh, Scotland, Abstract W97, 1994), who described enzymatic inactivation in transgenic tobacco via production of single-chain antibody fragments. Numerous other examples of insect resistance have been described. See, for example, U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658, 5,880,275; 5,763,245 and 5,763,241.

Resistance to Abiotic Stress

Abiotic stress includes dehydration or other osmotic stress, salinity, high or low light intensity, high or low temperatures, submergence, exposure to heavy metals, and oxidative stress. Delta-pyrroline-5-carboxylate synthetase (P5CS) from mothbean has been used to provide protection against general osmotic stress. Mannitol-1-phosphate dehydrogenase (mt1D) from *E. coli* has been used to provide protection against drought and salinity. Choline oxidase (codA from *Arthrobactor globiformis*) can protect against cold and salt. *E. coli* choline dehydrogenase (betA) provides protection against salt. Additional protection from cold can be provided by omega-3-fatty acid desaturase (fad7) from *Arabidopsis thaliana*. Trehalose-6-phosphate synthase and levan sucrase (SacB) from yeast and *Bacillus subtilis*, respectively, can provide protection against drought (summarized from Annex II Genetic Engineering for Abiotic Stress Tolerance in Plants, Consultative Group On International Agricultural Research Technical Advisory Committee). Overexpression of superoxide dismutase can be used to protect against superoxides, see U.S. Pat. No. 5,538,878.

Additional Traits

Additional traits can be introduced into the hemp variety of the present invention. A non-limiting example of such a trait is a coding sequence which decreases RNA and/or protein levels. The decreased RNA and/or protein levels may be achieved through RNAi methods, such as those described in U.S. Pat. No. 6,506,559.

Another trait that may find use with the hemp variety of the invention is a sequence which allows for site-specific recombination. Examples of such sequences include the FRT sequence used with the FLP recombinase (Zhu and Sadowski, *J. Biol. Chem.*, 270:23044-23054, 1995) and the LOX sequence used with CRE recombinase (Sauer, *Mol. Cell. Biol.*, 7:2087-2096, 1987). The recombinase genes can be encoded at any location within the genome of the hemp plant and are active in the hemizygous state.

In certain embodiments hemp plants may be made more tolerant to or more easily transformed with *Agrobacterium tumefaciens*. For example, expression of p53 and iap, two baculovirus cell-death suppressor genes, inhibited tissue necrosis and DNA cleavage. Additional targets may include plant-encoded proteins that interact with the *Agrobacterium* Vir genes; enzymes involved in plant cell wall formation; and histones, histone acetyltransferases and histone deacetylases (reviewed in Gelvin, *Microbiology &Mol. Biol. Reviews*, 67:16-37, 2003).

In addition to the modification of oil, fatty acid, or phytate content described above, certain embodiments may modify the amounts or levels of other compounds. For example, the amount or composition of antioxidants can be altered. See, for example, U.S. Pat. Nos. 6,787,618 and 7,154,029 and International Patent Application Publication No. WO 00/68393, which disclose the manipulation of antioxidant levels, and International Patent Application Publication No. WO 03/082899, which discloses the manipulation of an antioxidant biosynthetic pathway.

Additionally, seed amino acid content may be manipulated. U.S. Pat. No. 5,850,016 and International Patent Application Publication No. WO 99/40209 disclose the alteration of the amino acid compositions of seeds. U.S. Pat. Nos. 6,080,913 and 6,127,600 disclose methods of increasing accumulation of essential amino acids in seeds.

U.S. Pat. No. 5,559,223 describes synthetic storage proteins of which the levels of essential amino acids can be manipulated. International Patent Application Publication No. WO 99/29882 discloses methods for altering amino acid content of proteins. International Patent Application Publication No. WO 98/20133 describes proteins with enhanced levels of essential amino acids. International Patent Application Publication No. WO 98/56935 and U.S. Pat. Nos. 6,346,403; 6,441,274; and 6,664,445 disclose plant amino acid biosynthetic enzymes. International Patent Application Publication No. WO 98/45458 describes synthetic seed proteins having a higher percentage of essential amino acids than wild-type.

U.S. Pat. No. 5,633,436 discloses plants comprising a higher content of sulfur-containing amino acids; U.S. Pat. No. 5,885,801 discloses plants comprising a high threonine content; U.S. Pat. Nos. 5,885,802 and 5,912,414 disclose plants comprising a high methionine content; U.S. Pat. No. 5,990,389 discloses plants comprising a high lysine content; U.S. Pat. No. 6,459,019 discloses plants comprising an increased lysine and threonine content; International Patent Application Publication No. WO 98/42831 discloses plants comprising a high lysine content; International Patent Application Publication No. WO 96/01905 discloses plants comprising a high threonine content; and International Patent Application Publication No. WO 95/15392 discloses plants comprising a high lysine content.

*Cannabis* Hemp Extracts and Compositions

In some embodiments, the present disclosure provides for extracts and compositions from the hemp plants of the present disclosure. *Cannabis* extracts or products or the present disclosure include:

Solvent reduced oils—also sometimes known as oil, BHO, $CO_2$ extract, among other names. This type of extract is made by soaking plant material in a chemical solvent capable of solubilizing one or more chemical constituents of the plant (e.g., cannabinoids and/or terpenes). After separating the solvent from plant material, the solvent can be boiled or evaporated off, leaving the extract "oil" behind. Butane Hash Oil is produced by passing butane over *Cannabis* and then letting the butane evaporate. Rick Simpson Oil is produced through isopropyl, or ethanol extraction of *Cannabis*. The resulting substance is a wax like golden brown paste. Another common extraction solvent for creating *Cannabis* oil is $CO_2$. Persons having skill in the art will be familiar with $CO_2$ extraction techniques and devices, including those disclosed in US 20160279183, US 2015/01505455, U.S. Pat. No. 9,730,911, and US 2018/0000857.

Heat extractions—The present disclosure also teaches extracts produced via heat-based extraction methods, such as those disclosed in US Patent Application Nos. US 2018/0078874, US 2019/0151771, US 2019/0076753, and U.S. Pat. No. 10,159,908, each of which is hereby incorporated by reference for all purposes. In some embodiments, the plants of the present disclosure can be extracted by exposing tissue to a hot air gas stream that volatizes cannabinoids and/or other secondary metabolites of the plant, which are then condensed and recovered in tanks.

In some embodiments, the present disclosure teaches exposing plants, plant parts or plant cells to vaporizing heat. As used herein, the term "vaporizing heat" refers to heat sufficient to volatize one or more terpene on cannabinoid components of said plant, plant part or plant cell. The boiling points for each of the cannabinoid and terpene constituents of a hemp plant are well known or readily ascertainable. In some embodiments, vaporizing heat comprises 150° F., 155° F., 160° F., 165° F., 170° F., 175° F., 180° F., 185° F., 190° F., 195° F., 200° F., 205° F., 210° F., 215° F., 220° F., 225° F., 230° F., 235° F., 240° F., 245° F., 250° F., 255° F., 260° F., 265° F., 270° F., 275° F., 280° F., 285° F., 290° F., 295° F., 300° F. ° F., 305° F. ° F., 310° F. ° F., 315° F. ° F., 320° F. ° F., 325° F. ° F., 330° F. ° F., 335° F. ° F., 340° F. ° F., 345° F., or 350° F., and all ranges and subranges therebetween.

Tinctures—are alcoholic extracts of *Cannabis*. These are usually made by mixing *Cannabis* material with high proof ethanol and separating out plant material. Within the dietary supplement industry "tincture" may also describe an oil dilution of hemp extract.

In some embodiments, the specialty *Cannabis* of the present disclosure is extracted via methods that preserve the cannabinoid and terpenes. In other embodiments, said methods can be used with any *Cannabis* plants. The extracts of the present disclosure are designed to produce products for human or animal consumption via inhalation (via combustion, vaporization and nebulization), buccal absorption within the mouth, oral administration (e.g., eating/drinking), and topical application delivery methods.

The chemical extraction of specialty *Cannabis* can be accomplished employing polar and non-polar solvents in various phases at varying pressures and temperatures to selectively or comprehensively extract terpenes, cannabinoids and other compounds of flavor, fragrance or pharmacological value for use individually or combination in the formulation of our products. The solvents employed for selective extraction of our cultivars may include water, carbon dioxide, 1,1,1,2-tetrafluoroethane, butane, propane, ethanol, isopropyl alcohol, hexane, and limonene, in combination or series. It is also possible to extract compounds of interest mechanically by sieving the plant parts that produce those compounds. Measuring the plant part, i.e. trichome gland head, to be sieved via optical or electron microscopy can aid the selection of the optimal sieve pore size, ranging from 30 to 130 microns, to capture the plant part of interest. The chemical and mechanical extraction methods of the present disclosure can be used to produce products that combine chemical extractions with plant parts containing compounds of interest.

The extracts of the present disclosure may also be combined with pure compounds of interest to the extractions, e.g. cannabinoids or terpenes to further enhance or modify the resulting formulation's fragrance, flavor or pharmacology. Thus, in some embodiments, the present disclosure teaches compositions comprising at least one ingredient extracted from the 'KIRSCHE' plant. In some embodiments, extracts from the hemp lines of the present disclosure are combined with one or more additional compounds. In some embodiments, extracts of the present disclosure, such as whole hemp extracts, or a purified cannabinoid from said hemp plant, can be combined with another cannabinoid or terpene to produce a composition.

The compositions of the present disclosure encompass many forms. In some embodiments, the present disclosure provides CBD oils and tinctures. In some embodiments, the present disclosure provides CBD capsules. In some embodiments, the present disclosure provides CBD infused edibles, such as gummies, gum, lollipops, taffy, cookies, brownies, ice cream, chocolate, jerky, animal dry and wet foods, animal treats, etc. In some embodiments, the present disclosure provides for cosmetics comprising CBD, such as lip stick, balms, creams, shampoo, conditioners, lotions, rubbing oils, lubricants, Etc. In some embodiments, the CBD oils comprise extracts from 'KIRSCHE', such as solvent extracted oils, heat extracted oils. In some embodiments, the capsules comprise extracts from 'KIRSCHE.'

In some embodiments, the present disclosure teaches hemp commodity products, including processed hemp inflorescences, fiber, hemp extract, cannabinoids, and terpenes. As used herein, the term "processed hemp inflorescences" means inflorescences from a hemp plant that have been harvested and dried to a moisture content of less than 20% wt/wt. In some embodiments, the processed hemp inflorescences are ground or broken up in smaller pieces.

Deposit Information

A deposit of the 'KIRSCHE' hemp cultivar is maintained by Charlotte's Web, Inc., 1600 Pearl St. Suite 300, Boulder Colo. 80302, USA. In addition, a sample of 2500 seeds of the 'KIRSCHE' variety of this disclosure have been deposited with an International Depositary Authority as established under the Budapest Treaty according to 37 CFR 1.803(a)(1). Applicant has deposited seeds at the Provasoli-Guillard National Center for Marine Algae and Microbiota (NCMA), located at the Bigelow Laboratory for Ocean Science at 60 Bigelow Drive East Boothbay, Me. 04544.

The 'KIRSCHE' seeds (a.k.a. WG-TR-F01bA-19) have been deposited and accepted under the Budapest Treaty as NCMA No. 202005042 on May 7, 2020.

To satisfy the enablement requirements of 35 U.S.C. 112, and to certify that the deposit of the isolated strain (i.e., hemp plant) of the present disclosure meets the criteria set forth in 37 C.F.R. 1.801-1.809 and Manual of Patent Examining Procedure (MPEP) 2402-2411.05, Applicants hereby make the following statements regarding the deposited 'KIRSCHE' hemp cultivar (deposited as NCMA No. 202005042):

1. During the pendency of this application, access to the disclosure will be afforded to the Commissioner upon request;
2. All restrictions on availability to the public will be irrevocably removed upon granting of the patent under conditions specified in 37 CFR 1.808;
3. The deposit will be maintained in a public repository for a period of 30 years or 5 years after the last request or for the effective life of the patent, whichever is longer;
4. A test of the viability of the biological material at the time of deposit will be conducted by the public depository under 37 C.F.R. 1.807; and
5. The deposit will be replaced if it should ever become unavailable.

Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 2,500 seeds of the same variety with the NCMA.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the non-limiting exemplary methods and materials are described herein.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. Nothing herein is to be construed as an admission that the present disclosure is not entitled to antedate such publication by virtue of prior disclosure.

Many modifications and other embodiments of the disclosures set forth herein will come to mind to one skilled in the art to which these disclosures pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. Although specific terms are employed herein, they are used in a generic and descriptive sense only and not for purposes of limitation.

While the disclosure has been described in connection with specific embodiments thereof, it will be understood that it is capable of further modifications and this application is intended to cover any variations, uses, or adaptations of the disclosure following, in general, the principles of the disclosure and including such departures from the present disclosure as come within known or customary practice within the art to which the disclosure pertains and as may be applied to the essential features hereinbefore set forth and as follows in the scope of the appended claims.

Example 1. Cannabinoid Potency Tests

Samples of inflorescences from the 'KIRSCHE' hemp line harvested at maturity were provided to a third party vendor for analysis. Six samples of the 'KIRSCHE' inflorescences were analyzed by using high performance liquid chromatography. The results of these analyses are provided below in Table 6.

TABLE 6

Cannabinoid Potency Analysis Results for 'KIRSCHE'

| Analysis | THC Potential | CBD Potential |
| --- | --- | --- |
| 1 | 0.24 | 8.77 |
| 2 | 0.26 | 9.93 |
| 3 | 0.26 | 8.46 |
| 4 | 0.27 | 9.79 |
| 5 | 0.27 | 9.78 |

Example 2. Terpene Profile Tests

Samples of inflorescences from the 'KIRSCHE' hemp line harvested at maturity were provided to a third party vendor for analysis. Three samples of the 'KIRSCHE' inflorescences were analyzed by using Gas Chromatography. The results of these analyses are provided below in Table 7.

TABLE 7

Terpene Profile Analysis Results for 'KIRSCHE'

| Compound | 1 % (w/w) | 2 % (w/w) | 3 % (w/w) |
| --- | --- | --- | --- |
| (−)-alpha-Bisabolol | 0.148 | 0.211 | 0.223 |
| Camphene | 0 | 0 | 0 |
| delta-3-Carene | 0 | 0 | 0 |
| beta-Caryophyllene | 0.193 | 0.215 | 0.224 |
| (−)-Caryophyllene Oxide | 0 | 0 | 0 |
| p-Cymene | 0 | 0 | 0 |
| Eucalyptol | 0.001 | 0.003 | 0.001 |
| Geraniol | 0 | 0 | 0 |
| alpha-Humulene | 0.077 | 0.088 | 0.09 |
| (−)-Isopulegol | 0 | 0 | 0 |
| d-Limonene | 0.01 | 0.007 | 0.011 |
| Linalool | 0 | 0 | 0 |
| beta-Myrcene | 0.025 | 0.019 | 0.027 |
| cis-Nerolidol | 0 | 0 | 0 |
| trans-Nerolidol | 0 | 0 | 0 |
| Ocimene | 0 | 0 | 0 |
| beta-Ocimene | 0.002 | 0.002 | 0.003 |
| alpha-Pinene | 0.009 | 0.007 | 0.007 |
| (−)-beta-Pinene | 0.006 | 0.005 | 0.005 |
| alpha-Terpinene | 0 | 0 | 0 |
| gamma-Terpinene | 0 | 0 | 0 |
| Terpinolene | 0 | 0 | 0 |

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment or any form of suggestion that they constitute valid prior art or form part of the common general knowledge in any country in the world.

NUMBERED EMBODIMENTS

Further embodiments contemplated by the disclosure are listed below.

1. A seed, plant, plant part, or plant cell of hemp plant variety designated 'KIRSCHE', wherein representative seed of the variety has been deposited under NCMA No. 202005042.

2. The hemp plant part of embodiment 1, wherein the plant part is an inflorescence.

3. A hemp plant or a plant part or a plant cell thereof, having all of the characteristics of the hemp plant variety designated 'KIRSCHE' listed in Tables 1-5.

4. A hemp plant, or a plant part or a plant cell thereof, having all of the essential physiological and morphological characteristics of the hemp plant of any one of embodiments 1-3.

5. A hemp plant, or a part or a plant cell thereof, having all of the essential physiological and morphological characteristics of the hemp plant variety designated 'KIRSCHE', wherein a representative sample of seed of said variety was deposited under NCMA No. 202005042.

6. A tissue culture of regenerable cells produced from the plant, plant part or plant cell of any one of embodiments 1-5, wherein a new plant regenerated from the tissue culture has all of the characteristics of the hemp plant variety designated 'KIRSCHE' listed in Tables 1-5 when grown under the same environmental conditions.

7. A hemp plant regenerated from the tissue culture of embodiment 6, said plant having all the characteristics of the hemp plant variety designated 'KIRSCHE' listed in Tables 1-5 when grown under the same environmental conditions.

8. A hemp plant regenerated from the tissue culture of embodiment 6, wherein the regenerated plant has all of the characteristics of the hemp plant variety designated 'KIRSCHE', wherein a representative sample of seed of said variety was deposited under NCMA No. 202005042.

9. A method for producing a hemp seed, comprising a) selfing the hemp plant of any one of embodiments 1-5 and 7-8, and b) harvesting the resultant hemp seed.

10. A hemp seed produced by the method of embodiment 9.

11. A method for producing a hemp seed comprising crossing the hemp plant of any one of embodiments 1-5 and 7-8 with a second, distinct plant.

12. An $F_1$ hemp seed produced by the method of embodiment 11.

13. An $F_1$ hemp plant, or a part or a plant cell thereof, produced by growing the seed of embodiment 12.

14. A method of producing a hemp plant derived from the variety 'KIRSCHE,' comprising: a) crossing the plant of any one of embodiments 1-5 and 7-8, with itself or a second plant to produce progeny seed; b) growing the progeny seed to produce a progeny plant and crossing the progeny plant with itself or a second plant to produce further progeny seed; and c) repeating steps (a) and (b) with sufficient inbreeding until a seed of an hemp plant derived from the variety 'KIRSCHE' is produced.

15. The method of embodiment 14, further comprising crossing the hemp plant derived from the variety 'KIRSCHE,' with a plant of a different genotype to produce seed of a hybrid plant derived from the hemp variety 'KIRSCHE.'

16. A method for producing nucleic acids, the method comprising isolating nucleic acids from the seed, plant, plant part, or plant cell of any one of embodiments 1-15.

17. The hemp plant of any one of embodiments 1-5 and 7-8, comprising a single locus conversion and otherwise essentially all of the characteristics of the hemp plant of any one of embodiments 1-5 and 7-8 when grown in the same environmental conditions.

18. The hemp plant of embodiment 17, wherein the single locus conversion confers said plant with herbicide resistance.

19. The hemp plant of embodiment 17, wherein the single locus conversion is an artificially mutated gene or nucleotide sequence.

20. The hemp plant of embodiment 17, wherein the single locus conversion is a gene that has been modified through the use of breeding techniques.

21. A cultivar of hemp designated 'KIRSCHE' as described and detailed herein.

22. A method of producing a cannabinoid extract, said method comprising the steps a) contacting the plant of any one of embodiments 1-5 and 7-8 with a solvent, thereby producing a cannabinoid extract.

23. A dry, sinsemilla non-viable plant or part thereof, wherein seed of hemp plants producing said dry plant and part thereof has been deposited under NCMA No. 202005042.

24. An assemblage of dry, non-viable sinsemilla female inflorescences from a hemp plant variety designated 'KIRSCHE' wherein representative seed of the variety has been deposited under NCMA No. 202005042.

25. The dry, non-viable plant part of embodiment 23 or 24, wherein the plant part is an inflorescence.

26. The dry, non-viable plant part of embodiment 23 or 24, wherein the plant part is a trichome.

27. Dry, non-viable kief powder comprising cannabidiol (CBD), wherein seed of hemp plants producing said kief has been deposited under NCMA No. 202005042.

28. A method of producing a hemp plant with cannabidiol (CBD), said method comprising propagating a vegetative cutting from a hemp plant variety designated 'KIRSCHE' wherein representative seed of the variety has been deposited under NCMA No. 202005042.

29. The hemp plant with CBD, produced according to the methods of embodiment 28.

30. The hemp plant of embodiment 5, wherein the plant is asexually reproduced.

31. A method for producing a hemp plant with inflorescences that produce cannabidiol (CBD), said method comprising:
propagating a vegetative cutting from a stock hemp plant, thereby producing the hemp plant having CBD;
wherein the stock hemp plant is a product of applying a plant breeding technique to a variety designated 'KIRSCHE', wherein representative seed of the variety has been deposited under NCMA No. 202005042.

32. The method of embodiment 31, wherein said plant breeding technique is recurrent selection.

33. The method of embodiment 31, wherein said plant breeding technique is mass selection.

34. The method of embodiment 31, wherein said plant breeding technique is hybridization.

35. The method of embodiment 31, wherein said plant breeding technique is open-pollination.

36. The method of embodiment 31, wherein said plant breeding technique is backcrossing.

37. The method of embodiment 31, wherein said plant breeding technique is pedigree breeding.

38. The method of embodiment 31, wherein said plant breeding technique is mutation breeding, and wherein said mutation selected is spontaneous or artificially induced.

39. A method for producing a *Cannabis* plant derived from a hemp variety designated 'KIRSCHE', said method comprising crossing 'KIRSCHE' with another *Cannabis* plant, thereby producing a progeny *Cannabis* plant; wherein representative seed of the 'KIRSCHE' variety has been deposited under NCMA No. 202005042.

40. The method of embodiment 39, further comprising the steps of:
a) crossing the progeny *Cannabis* plant from a previous step with itself or another *Cannabis* plant to produce a progeny *Cannabis* plant of a subsequent generation;
b) repeating step (a) for one or more additional generations to produce a *Cannabis* plant further derived from the hemp variety designated 'KIRSCHE'.

41. The method of embodiment 39 or 40, further comprising the step of contacting the *Cannabis* plant further derived from the hemp variety designated 'KIRSCHE' or a plant part derived therefrom with a solvent, or exposing said *Cannabis* plant or plant part to vaporizing heat, thereby producing a cannabinoid extract.

42. A method for producing a *Cannabis* plant derived from a hemp variety designated 'KIRSCHE', said method comprising:
propagating a vegetative cutting from a stock *Cannabis* plant, thereby producing the *Cannabis* plant derived from the hemp variety designated 'KIRSCHE';
wherein the stock *Cannabis* plant is a product of applying a plant breeding technique to 'KIRSCHE', wherein representative seed of the 'KIRSCHE' variety has been deposited under NCMA No. 202005042.

43. The method of embodiment 42, further comprising the step of contacting the *Cannabis* plant derived from the hemp variety designated 'KIRSCHE' or a plant part derived therefrom with a solvent, or exposing said *Cannabis* plant or plant part to vaporizing heat, thereby producing a cannabinoid extract.

44. The method of embodiment 42, wherein said plant breeding technique is recurrent selection.

45. The method of embodiment 42, wherein said plant breeding technique is mass selection.

46. The method of embodiment 42, wherein said plant breeding technique is hybridization.

47. The method of embodiment 42, wherein said plant breeding technique is open-pollination.

48. The method of embodiment 42, wherein said plant breeding technique is backcrossing.

49. The method of embodiment 42, wherein said plant breeding technique is pedigree breeding.

50. The method of embodiment 42, wherein said plant breeding technique is mutation breeding, and wherein said mutation selected is spontaneous or artificially induced.

51. The method of embodiment 42, wherein said plant breeding technique is marker enhanced selection.

52. A method for producing a *Cannabis* plant derived from a hemp variety designated 'KIRSCHE', said method comprising:
crossing a stock *Cannabis* plant with itself or another *Cannabis* plant, thereby producing the *Cannabis* plant derived from the hemp variety designated 'KIRSCHE';
wherein the stock *Cannabis* plant is a product of applying a plant breeding technique to 'KIRSCHE', wherein representative seed of the 'KIRSCHE' variety has been deposited under NCMA No. 202005042.

53. The method of embodiment 52, further comprising the step of contacting the *Cannabis* plant derived from the hemp variety designated 'KIRSCHE' or a plant part derived therefrom with a solvent, or exposing said *Cannabis* plant or plant part to vaporizing heat, thereby producing a cannabinoid extract.

54. The method of embodiment 52, wherein said plant breeding technique is recurrent selection.

55. The method of embodiment 52, wherein said plant breeding technique is mass selection.

56. The method of embodiment 52, wherein said plant breeding technique is hybridization.

57. The method of embodiment 52, wherein said plant breeding technique is open-pollination.

58. The method of embodiment 52, wherein said plant breeding technique is backcrossing.

59. The method of embodiment 52, wherein said plant breeding technique is pedigree breeding.

60. The method of embodiment 52, wherein said plant breeding technique is mutation breeding, and wherein said mutation selected is spontaneous or artificially induced.

61. The method of embodiment 52, wherein said plant breeding technique is marker enhanced selection.

62. The hemp plant of embodiment 5, wherein the plant is capable of producing an asexual clone of said hemp plant.

63. The hemp plant of embodiment 62, wherein the asexual clone is capable of producing said hemp plant of embodiment 1.

64. A method of producing a commodity plant product, the method comprising producing the commodity plant product from the plant of embodiment 1.

65. A method of producing a commodity plant product comprising collecting the commodity plant product from a seed, plant, plant part, or plant cell of hemp plant variety designated 'KIRSCHE', wherein representative seed of the variety has been deposited under NCMA No. 202005042

66. The method of embodiments 64 or 65, wherein the commodity plant product is selected from a group consisting of processed hemp inflorescence, hemp fiber, hemp oil extract, terpenes, and cannabinoids.

What is claimed is:

1. A seed, plant, plant part, or plant cell of a hemp plant variety designated 'KIRSCHE', wherein seed of the variety has been deposited under NCMA No. 202005042.

2. The plant part of claim 1, wherein the plant part is selected from the group consisting of a leaf, a stem, an inflorescence, and a trichome.

3. The plant part of claim 1, wherein the plant part is an inflorescence.

4. A tissue culture of regenerable cells produced from the plant, plant part, or plant cell of claim 1.

5. A hemp plant regenerated from the tissue culture of claim 4, said plant having all the morphological and physiological characteristics of the hemp plant variety designated 'KIRSCHE' deposited under NCMA No. 202005042, when grown under the same environmental conditions.

6. A method for producing nucleic acids, the method comprising isolating nucleic acids from the seed, plant, plant part, or plant cell of claim 1.

7. The plant, plant part, or plant cell of claim 1, further comprising a single locus conversion and otherwise all of the essential morphological and physiological characteristics of the hemp plant variety designated 'KIRSCHE' deposited under NCMA No. 202005042, when grown under the same environmental conditions.

8. The plant, plant part, or plant cell of claim 7, wherein the single locus conversion comprises a transgene.

9. A seed that produces the plant of claim 8.

10. The plant, plant part, or plant cell of claim 7, wherein the single locus conversion confers a trait selected from the group consisting of male sterility, herbicide tolerance, insect resistance, pest resistance, disease resistance, and abiotic stress resistance.

11. The plant, plant part, or plant cell of claim 7, wherein the single locus that confers herbicide tolerance confers tolerance to benzonitrile herbicides, cyclohexanedione herbicides, imidazolinone herbicides, phenoxy herbicides, sulfonylurea herbicides, triazine herbicides, 1-aminocyclopropane-1-carboxylic acid synthase-inhibiting herbicides, 4-hydroxyphenylpyruvate dioxygenase-inhibiting herbicides, acetolactate synthase-inhibiting herbicides, protoporphyrinogen oxidase-inhibiting herbicides, 2,4-dichlorophenoxyacetic acid (2,4-D), bromoxynil, dicamba, glufosinate, glyphosate, nicosulfuron, or quizalofop-p-ethyl.

12. A method of producing a commodity plant product, the method comprising producing the commodity plant product from the plant, plant part, or plant cell of claim 1.

13. The method of claim 12, wherein the commodity plant product is selected from a group consisting of processed hemp inflorescence, hemp fiber, hemp oil extract, terpenes, and cannabinoids.

14. A method of producing a cannabinoid extract, said method comprising the step of contacting the plant, plant part, or plant cell of claim 1 with a solvent, or exposing said plant, plant part, or plant cell to vaporizing heat, thereby producing a cannabinoid extract.

15. A method of producing a hemp plant, comprising placing the seed of claim 1 in conditions conducive to germination, thereby producing a hemp plant.

16. A method of producing a hemp plant with cannabidiol (CBD), said method comprising propagating a vegetative cutting from a hemp plant variety designated 'KIRSCHE', wherein said hemp plant has all the morphological and physiological characteristics of variety 'KIRSCHE' deposited under NCMA No. 202005042.

17. A method for producing a progeny *Cannabis* seed, comprising crossing the hemp plant of claim 1, with itself or with another plant, thereby producing a progeny *Cannabis* seed.

18. The method of claim 17, further comprising the step of growing the progeny *Cannabis* seed to produce a progeny *Cannabis* plant.

19. The method of claim 18, further comprising the steps of:
   a) crossing the progeny *Cannabis* plant from a previous step with itself or another *Cannabis* plant to produce a progeny *Cannabis* plant of a subsequent generation;
   b) repeating step (a) for one or more additional generations to produce a *Cannabis* plant further derived from the hemp variety designated 'KIRSCHE'.

20. The method of claim 19, further comprising the step of contacting the *Cannabis* plant further derived from the hemp variety designated 'KIRSCHE' or a plant part derived therefrom with a solvent, or exposing said *Cannabis* plant or plant part to vaporizing heat, thereby producing a cannabinoid extract.

21. A method for producing a *Cannabis* plant derived from a hemp variety designated 'KIRSCHE', said method comprising:
   propagating a vegetative cutting from a stock *Cannabis* plant, thereby producing the *Cannabis* plant derived from the hemp variety designated 'KIRSCHE';
wherein the stock *Cannabis* plant is a product of applying a plant breeding technique to 'KIRSCHE', wherein seed of the 'KIRSCHE' variety has been deposited under NCIMB No. 202005042.

22. The method of claim 21, further comprising the step of contacting the *Cannabis* plant derived from the hemp variety designated 'KIRSCHE' or a plant part derived therefrom with a solvent, or exposing said *Cannabis* plant or plant part to vaporizing heat, thereby producing a cannabinoid extract.

23. A method for producing a *Cannabis* plant derived from a hemp variety designated 'KIRSCHE', said method comprising:
   crossing a stock *Cannabis* plant with itself or another *Cannabis* plant, thereby producing the *Cannabis* plant derived from the hemp variety designated 'KIRSCHE';
wherein the stock *Cannabis* plant is a product of applying a plant breeding technique to 'KIRSCHE', wherein seed of the 'KIRSCHE' variety has been deposited under NCIMB No. 202005042.

24. The method of claim 23, further comprising the step of contacting the *Cannabis* plant derived from the hemp variety designated 'KIRSCHE' or a plant part derived therefrom with a solvent, or exposing said *Cannabis* plant or plant part to vaporizing heat, thereby producing a cannabinoid extract.

25. The method of claim 23, wherein said plant breeding technique is recurrent selection.

26. The method of claim 23, wherein said plant breeding technique is mass selection.

27. The method of claim 23, wherein said plant breeding technique is hybridization.

28. The method of claim 23, wherein said plant breeding technique is open-pollination.

29. The method of claim 23, wherein said plant breeding technique is backcrossing.

* * * * *

UNITED STATES PATENT AND TRADEMARK OFFICE
CERTIFICATE OF CORRECTION

PATENT NO. : 10,888,060 B1
APPLICATION NO. : 16/895569
DATED : January 12, 2021
INVENTOR(S) : Keri Reel Page 1 of 1

It is certified that error appears in the above-identified patent and that said Letters Patent is hereby corrected as shown below:

In the Claims

Claim 21, at Column 42, Line 18, "NCIMB" should read --NCMA--

Claim 23, at Column 42, Line 34, "NCIMB" should read --NCMA--

Signed and Sealed this
Twenty-ninth Day of March, 2022

Drew Hirshfeld
*Performing the Functions and Duties of the*
*Under Secretary of Commerce for Intellectual Property and*
*Director of the United States Patent and Trademark Office*